(12) United States Patent
Chapman, Jr. et al.

(10) Patent No.: US 11,278,654 B2
(45) Date of Patent: Mar. 22, 2022

(54) PNEUMATIC MANIFOLD FOR A DIALYSIS SYSTEM

(71) Applicant: Medtronic, Inc., Minneapolis, MN (US)

(72) Inventors: Paul R. Chapman, Jr., Lutz, FL (US); William Hajko, Safety Harbor, FL (US); Carl Wilbert Gomes, II, Parrish, FL (US)

(73) Assignee: Medtronic, Inc., Minneapolis, MN (US)

( * ) Notice: Subject to any disclaimer, the term of this patent is extended or adjusted under 35 U.S.C. 154(b) by 842 days.

(21) Appl. No.: 16/149,246

(22) Filed: Oct. 2, 2018

(65) Prior Publication Data

US 2019/0175814 A1   Jun. 13, 2019

Related U.S. Application Data

(60) Provisional application No. 62/595,859, filed on Dec. 7, 2017.

(51) Int. Cl.
*A61M 1/36* (2006.01)
*A61M 1/16* (2006.01)
(Continued)

(52) U.S. Cl.
CPC ........ *A61M 1/3627* (2013.01); *A61M 1/1601* (2014.02); *A61M 1/3624* (2013.01); *A61M 1/3639* (2013.01); *A61M 39/24* (2013.01); *A61M 39/28* (2013.01); *A61M 1/14* (2013.01); *A61M 2039/226* (2013.01); *A61M 2205/07* (2013.01); *A61M 2205/128* (2013.01);
(Continued)

(58) Field of Classification Search
CPC .............. A61M 1/3627; A61M 1/1601; A61M 1/3624; A61M 39/24; A61M 39/28; A61M 1/14; A61M 2039/226; A61M 2205/07; A61M 2205/128; A61M 2205/3334; A61M 2205/3379; A61M 2205/3389; A61M 2205/75
USPC ........................................................ 604/6.01
See application file for complete search history.

(56) References Cited

U.S. PATENT DOCUMENTS

| 3,091,098 A | 5/1963 | Bowers |
| 3,370,710 A | 2/1968 | Bluemle |

(Continued)

FOREIGN PATENT DOCUMENTS

| CN | 101687070 | 3/2010 |
| CN | 101883594 A | 11/2010 |

(Continued)

OTHER PUBLICATIONS

Extended European Search Report for App. No. 20203585.3, dated Feb. 17, 2021.

(Continued)

*Primary Examiner* — Andrew J Mensh

(57) ABSTRACT

The invention relates to a pneumatic manifold for controlling a fluid level in an arterial and/or venous drip chamber of a dialysis system. The pneumatic manifold includes pneumatic valves fluidly connected to conduits and one or more pumps. Selectively activating the pneumatic valves can result in pressure changes for raising or lowering a fluid level in the arterial and/or venous drip chambers.

21 Claims, 8 Drawing Sheets

(51) Int. Cl.
*A61M 39/24* (2006.01)
*A61M 39/22* (2006.01)
*A61M 39/28* (2006.01)
*A61M 1/14* (2006.01)

(52) U.S. Cl.
CPC .............. *A61M 2205/3334* (2013.01); *A61M 2205/3379* (2013.01); *A61M 2205/3389* (2013.01); *A61M 2205/75* (2013.01)

(56) References Cited

U.S. PATENT DOCUMENTS

| | | | |
|---|---|---|---|
| 3,506,126 A | 4/1970 | Lindsay, Jr. | |
| 3,608,729 A | 9/1971 | Haselden | |
| 3,669,878 A | 6/1972 | Marantz | |
| 3,669,880 A | 6/1972 | Marantz | |
| 3,692,648 A | 9/1972 | Matloff | |
| 3,776,819 A | 12/1973 | Williams | |
| 3,809,241 A | 5/1974 | Alvine | |
| 3,850,835 A | 11/1974 | Marantz | |
| 3,884,808 A | 5/1975 | Scott | |
| 3,902,490 A | 9/1975 | Jacobsen | |
| 3,939,069 A | 2/1976 | Granger | |
| 3,989,622 A | 11/1976 | Marantz | |
| 4,060,485 A | 11/1977 | Eaton | |
| 4,094,775 A | 6/1978 | Mueller | |
| 4,136,708 A | 1/1979 | Cosentino | |
| 4,142,845 A | 3/1979 | Lepp | |
| 4,201,555 A | 5/1980 | Tkach | |
| 4,209,392 A | 6/1980 | Wallace | |
| 4,269,708 A | 5/1981 | Bonomini | |
| 4,316,725 A | 2/1982 | Hovind | |
| 4,371,385 A | 2/1983 | Johnson | |
| 4,374,382 A | 2/1983 | Markowitz | |
| 4,376,707 A | 3/1983 | Lehmann | |
| 4,381,999 A | 5/1983 | Boucher | |
| 4,430,098 A | 2/1984 | Bowman | |
| 4,460,555 A | 7/1984 | Thompson | |
| 4,490,135 A | 12/1984 | Troutner | |
| 4,556,063 A | 12/1985 | Thompson | |
| 4,562,751 A | 1/1986 | Nason | |
| 4,581,141 A | 4/1986 | Ash | |
| 4,612,122 A | 9/1986 | Ambrus | |
| 4,650,587 A | 3/1987 | Polak | |
| 4,678,408 A | 7/1987 | Mason | |
| 4,685,903 A | 8/1987 | Cable | |
| 4,695,385 A | 9/1987 | Boag | |
| 4,715,398 A | 12/1987 | Shouldice | |
| 4,747,822 A | 5/1988 | Peabody | |
| 4,750,494 A | 6/1988 | King | |
| 4,816,162 A | 3/1989 | Rosskopf et al. | |
| 4,826,663 A | 5/1989 | Alberti | |
| 4,828,693 A | 5/1989 | Lindsay | |
| 4,885,001 A | 12/1989 | Leppert | |
| 4,900,308 A | 2/1990 | Verkaart | |
| 4,915,713 A | 4/1990 | Buzza | |
| 4,950,230 A | 8/1990 | Kendell | |
| 4,977,888 A | 12/1990 | Rietter | |
| 5,015,388 A | 5/1991 | Pusineri | |
| 5,032,265 A | 7/1991 | Jha | |
| 5,080,653 A | 1/1992 | Voss | |
| 5,092,886 A | 3/1992 | Dobos-Hardy | |
| 5,097,122 A | 3/1992 | Coiman | |
| 5,114,580 A | 5/1992 | Ahmad | |
| 5,127,404 A | 7/1992 | Wyborny | |
| 5,141,493 A | 8/1992 | Jacobsen | |
| 5,180,403 A | 1/1993 | Kogure | |
| 5,192,132 A | 3/1993 | Pelensky | |
| 5,230,702 A | 7/1993 | Lindsay | |
| 5,284,470 A | 2/1994 | Beltz | |
| 5,302,288 A | 4/1994 | Meidl | |
| 5,305,745 A | 4/1994 | Zacouto | |
| 5,308,315 A | 5/1994 | Khuri | |
| 5,318,750 A | 6/1994 | Lascombes | |
| 5,399,157 A | 3/1995 | Goux | |
| 5,419,347 A | 5/1995 | Carruth | |
| 5,441,049 A | 8/1995 | Masano | |
| 5,442,969 A | 8/1995 | Troutner | |
| 5,468,388 A | 11/1995 | Goddard | |
| 5,507,723 A | 4/1996 | Keshaviah | |
| 5,591,344 A | 1/1997 | Kenley | |
| 5,643,201 A | 7/1997 | Peabody | |
| 5,662,806 A | 9/1997 | Keshaviah et al. | |
| 5,683,432 A | 11/1997 | Goedeke | |
| 5,685,835 A | 11/1997 | Brugger | |
| 5,685,988 A | 11/1997 | Malchesky | |
| 5,702,536 A | 12/1997 | Carruth | |
| 5,744,031 A | 4/1998 | Bene | |
| 5,762,782 A | 6/1998 | Kenley | |
| 5,849,179 A | 12/1998 | Emerson | |
| 5,858,186 A | 1/1999 | Glass | |
| 5,863,421 A | 1/1999 | Peter | |
| 5,938,938 A | 8/1999 | Bosetto | |
| 5,944,684 A | 8/1999 | Roberts | |
| 5,948,251 A | 9/1999 | Brugger | |
| 6,048,732 A | 4/2000 | Anslyn | |
| 6,052,622 A | 4/2000 | Holmstrom | |
| 6,058,331 A | 5/2000 | King | |
| 6,114,176 A | 9/2000 | Edgson et al. | |
| 6,126,831 A | 10/2000 | Goldau | |
| 6,171,480 B1 | 1/2001 | Lee | |
| 6,230,059 B1 | 5/2001 | Duffin | |
| 6,248,093 B1 | 6/2001 | Moberg | |
| 6,251,167 B1 | 6/2001 | Berson | |
| 6,254,567 B1 | 7/2001 | Treu | |
| 6,264,680 B1 | 7/2001 | Ash | |
| 6,315,707 B1* | 11/2001 | Smith | B04B 5/0442 |
| | | | 210/782 |
| 6,321,101 B1 | 11/2001 | Holmstrom | |
| 6,362,591 B1 | 3/2002 | Moberg | |
| 6,363,279 B1 | 3/2002 | Ben-Haim | |
| 6,521,184 B1 | 2/2003 | Edgson et al. | |
| 6,554,798 B1 | 4/2003 | Mann | |
| 6,555,986 B2 | 4/2003 | Moberg | |
| 6,589,229 B1 | 7/2003 | Connelly | |
| 6,593,747 B2 | 7/2003 | Puskas | |
| 6,602,399 B1 | 8/2003 | Fromherz | |
| 6,627,164 B1 | 9/2003 | Wong | |
| 6,666,840 B1 | 12/2003 | Falkvall et al. | |
| 6,676,608 B1 | 1/2004 | Keren | |
| 6,711,439 B1 | 3/2004 | Bradley | |
| 6,719,745 B1 | 4/2004 | Taylor | |
| 6,726,647 B1 | 4/2004 | Sternby | |
| 6,780,322 B1 | 8/2004 | Bissler | |
| 6,814,724 B2 | 11/2004 | Taylor | |
| 6,818,196 B2 | 11/2004 | Wong | |
| 6,824,524 B1 | 11/2004 | Favre | |
| 6,861,266 B1 | 3/2005 | Sternby | |
| 6,878,283 B2 | 4/2005 | Thompson | |
| 6,960,179 B2 | 11/2005 | Gura | |
| 7,023,359 B2 | 4/2006 | Goetz | |
| 7,033,498 B2 | 4/2006 | Wong | |
| 7,074,332 B2 | 7/2006 | Summerton | |
| 7,077,819 B1 | 7/2006 | Goldau | |
| 7,097,630 B2 | 8/2006 | Gotch | |
| 7,101,519 B2 | 9/2006 | Wong | |
| 7,153,693 B2 | 12/2006 | Tajiri | |
| 7,169,303 B2 | 1/2007 | Sullivan | |
| 7,208,092 B2 | 4/2007 | Micheli | |
| 7,241,272 B2 | 7/2007 | Karoor | |
| 7,276,042 B2 | 10/2007 | Polaschegg | |
| 7,279,031 B1 | 10/2007 | Wright | |
| 7,318,892 B2* | 1/2008 | Connell | A61M 1/1684 |
| | | | 210/94 |
| 7,326,576 B2 | 2/2008 | Womble et al. | |
| 7,435,342 B2 | 10/2008 | Tsukamoto | |
| 7,488,447 B2 | 2/2009 | Sternby | |
| 7,500,958 B2 | 3/2009 | Asbrink | |
| 7,537,688 B2 | 5/2009 | Tarumi | |
| 7,544,300 B2 | 6/2009 | Brugger | |
| 7,544,737 B2 | 6/2009 | Poss | |
| 7,563,240 B2 | 7/2009 | Gross | |
| 7,566,432 B2 | 7/2009 | Wong | |
| 7,575,564 B2 | 8/2009 | Childers | |

(56) References Cited

U.S. PATENT DOCUMENTS

| | | |
|---|---|---|
| 7,597,806 B2 | 10/2009 | Uchi |
| 7,674,231 B2 | 3/2010 | McCombie |
| 7,704,361 B2 | 4/2010 | Garde |
| 7,736,507 B2 | 6/2010 | Wong |
| 7,744,553 B2 | 6/2010 | Kelly |
| 7,754,852 B2 | 7/2010 | Burnett |
| 7,756,572 B1 | 7/2010 | Fard |
| 7,776,210 B2 | 8/2010 | Rosenbaum |
| 7,785,463 B2 | 8/2010 | Bissler |
| 7,790,103 B2 | 9/2010 | Shah |
| 7,794,141 B2 | 9/2010 | Perry |
| 7,794,419 B2 | 9/2010 | Paolini |
| 7,850,635 B2 | 12/2010 | Polaschegg |
| 7,857,976 B2 | 12/2010 | Bissler |
| 7,867,214 B2 | 1/2011 | Childers |
| 7,896,831 B2 | 3/2011 | Sternby |
| 7,922,686 B2 | 4/2011 | Childers |
| 7,922,911 B2 | 4/2011 | Micheli |
| 7,947,179 B2 | 5/2011 | Rosenbaum |
| 7,955,290 B2 | 6/2011 | Karoor |
| 7,955,291 B2 | 6/2011 | Sternby |
| 7,967,022 B2 | 6/2011 | Grant |
| 7,981,082 B2 | 7/2011 | Wang |
| 7,988,854 B2 | 8/2011 | Tsukamoto |
| 8,002,726 B2 | 8/2011 | Karoor |
| 8,029,454 B2 | 10/2011 | Kelly |
| 8,034,161 B2 | 10/2011 | Gura |
| 8,066,658 B2 | 11/2011 | Karoor |
| 8,070,709 B2 | 12/2011 | Childers |
| 8,080,161 B2 | 12/2011 | Ding et al. |
| 8,087,303 B2 | 1/2012 | Beavis |
| 8,096,969 B2 | 1/2012 | Roberts |
| 8,105,265 B2 * | 1/2012 | Demers ............... A61M 1/3666 604/6.15 |
| 8,137,553 B2 | 3/2012 | Fulkerson |
| 8,180,574 B2 | 5/2012 | Lo |
| 8,183,046 B2 | 5/2012 | Lu |
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,292,594 B2 | 10/2012 | Tracey |
| 8,303,532 B2 | 11/2012 | Hamada |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,404,491 B2 | 3/2013 | Li |
| 8,409,441 B2 | 4/2013 | Wilt |
| 8,409,444 B2 | 4/2013 | Wong |
| 8,449,487 B2 | 5/2013 | Hovland |
| 8,491,517 B2 | 7/2013 | Karoor |
| 8,496,809 B2 | 7/2013 | Roger |
| 8,499,780 B2 | 8/2013 | Wilt |
| 8,500,672 B2 | 8/2013 | Caleffi |
| 8,500,676 B2 | 8/2013 | Jansson |
| 8,500,994 B2 | 8/2013 | Weaver |
| 8,512,271 B2 | 8/2013 | Moissl |
| 8,518,258 B2 | 8/2013 | Balschat |
| 8,518,260 B2 | 8/2013 | Raimann |
| 8,521,482 B2 | 8/2013 | Akonur |
| 8,535,525 B2 | 9/2013 | Heyes |
| 8,560,510 B2 | 10/2013 | Brueggerhoff |
| 8,562,822 B2 | 10/2013 | Roger |
| 8,580,112 B2 | 11/2013 | Updyke |
| 8,597,227 B2 | 12/2013 | Childers |
| 8,696,626 B2 | 4/2014 | Kirsch |
| 8,777,892 B2 | 7/2014 | Sandford |
| 8,903,492 B2 | 12/2014 | Soykan |
| 8,906,240 B2 | 12/2014 | Crnkovich |
| 9,144,640 B2 | 9/2015 | Pudil |
| 9,173,987 B2 | 11/2015 | Meyer |
| 2002/0027106 A1 | 3/2002 | Smith |
| 2002/0042561 A1 | 4/2002 | Schulman |
| 2002/0045851 A1 | 4/2002 | Suzuki |
| 2002/0104800 A1 | 8/2002 | Collins |
| 2002/0112609 A1 | 8/2002 | Wong |
| 2003/0010717 A1 | 1/2003 | Brugger |
| 2003/0080059 A1 | 5/2003 | Peterson |
| 2003/0097086 A1 | 5/2003 | Gura |
| 2003/0105424 A1 | 6/2003 | Karoor |
| 2003/0105435 A1 | 6/2003 | Taylor |
| 2003/0114787 A1 | 6/2003 | Gura |
| 2004/0019312 A1 | 1/2004 | Childers |
| 2004/0019320 A1 | 1/2004 | Childers |
| 2004/0068219 A1 | 4/2004 | Summerton |
| 2004/0082903 A1 | 4/2004 | Micheli |
| 2004/0099593 A1 | 5/2004 | DePaolis |
| 2004/0102732 A1 | 5/2004 | Naghavi |
| 2004/0143173 A1 | 7/2004 | Reghabi |
| 2004/0147900 A1 | 7/2004 | Polaschegg |
| 2004/0168969 A1 | 9/2004 | Sternby |
| 2004/0215090 A1 | 10/2004 | Erkkila |
| 2005/0006296 A1 | 1/2005 | Sullivan |
| 2005/0065760 A1 | 3/2005 | Murtfeldt |
| 2005/0101901 A1 | 5/2005 | Gura |
| 2005/0113796 A1 | 5/2005 | Taylor |
| 2005/0115898 A1 | 6/2005 | Sternby |
| 2005/0126961 A1 | 6/2005 | Bissler |
| 2005/0131331 A1 * | 6/2005 | Kelly .................. A61M 1/3434 604/4.01 |
| 2005/0131332 A1 * | 6/2005 | Kelly .................. A61M 1/1613 604/4.01 |
| 2005/0153904 A1 | 6/2005 | Fager |
| 2005/0126998 A1 | 7/2005 | Childers |
| 2005/0148923 A1 | 7/2005 | Sternby |
| 2005/0150832 A1 | 7/2005 | Tsukamoto |
| 2005/0234381 A1 | 10/2005 | Niemetz |
| 2005/0274658 A1 | 12/2005 | Rosenbaum |
| 2006/0025661 A1 | 2/2006 | Sweeney |
| 2006/0217771 A1 | 2/2006 | Soykan |
| 2006/0054489 A1 | 3/2006 | Denes |
| 2006/0076295 A1 | 4/2006 | Leonard |
| 2006/0157335 A1 | 7/2006 | Levine |
| 2006/0157413 A1 | 7/2006 | Bene |
| 2006/0186044 A1 | 8/2006 | Nalesso |
| 2006/0195064 A1 | 8/2006 | Plahey |
| 2006/0226079 A1 | 10/2006 | Mori |
| 2006/0241709 A1 | 10/2006 | Soykan |
| 2006/0264894 A1 | 11/2006 | Moberg |
| 2007/0007208 A1 | 1/2007 | Brugger |
| 2007/0066928 A1 | 3/2007 | Lannoy |
| 2007/0072285 A1 | 3/2007 | Barringer |
| 2007/0138011 A1 | 6/2007 | Hofmann |
| 2007/0175827 A1 | 8/2007 | Wariar |
| 2007/0179431 A1 | 8/2007 | Roberts |
| 2007/0213653 A1 | 9/2007 | Childers |
| 2007/0213665 A1 | 9/2007 | Curtin |
| 2007/0215545 A1 | 9/2007 | Bissler |
| 2007/0243113 A1 | 10/2007 | DiLeo |
| 2007/0255250 A1 | 11/2007 | Moberg |
| 2008/0006570 A1 | 1/2008 | Gura |
| 2008/0015493 A1 | 1/2008 | Childers et al. |
| 2008/0021337 A1 | 1/2008 | Li |
| 2008/0051696 A1 | 2/2008 | Curtin |
| 2008/0053905 A9 | 3/2008 | Brugger |
| 2008/0067132 A1 | 3/2008 | Ross |
| 2008/0093276 A1 | 4/2008 | Roger |
| 2008/0154543 A1 | 6/2008 | Rajagopal |
| 2008/0215247 A1 | 9/2008 | Tonelli |
| 2008/0217245 A1 | 9/2008 | Rambod |
| 2008/0230473 A1 | 9/2008 | Herbst |
| 2008/0253427 A1 | 10/2008 | Kamen |
| 2009/0012450 A1 | 1/2009 | Shah |
| 2009/0020471 A1 | 1/2009 | Tsukamoto |
| 2009/0078636 A1 | 3/2009 | Uchi |
| 2009/0084199 A1 | 4/2009 | Wright |
| 2009/0084721 A1 | 4/2009 | Yardimci |
| 2009/0101549 A1 | 4/2009 | Kamen |
| 2009/0101552 A1 | 4/2009 | Fulkerson |
| 2009/0101577 A1 | 4/2009 | Fulkerson |
| 2009/0105629 A1 | 4/2009 | Grant |

(56) References Cited

U.S. PATENT DOCUMENTS

| | | |
|---|---|---|
| 2009/0107335 A1 | 4/2009 | Wilt |
| 2009/0112151 A1* | 4/2009 | Chapman ............ F15B 13/0832 604/29 |
| 2009/0120864 A1 | 5/2009 | Fulkerson |
| 2009/0124963 A1 | 5/2009 | Hogard |
| 2009/0127193 A1 | 5/2009 | Updyke |
| 2009/0131858 A1 | 5/2009 | Fissell |
| 2009/0159527 A1 | 6/2009 | Mickols |
| 2009/0171261 A1 | 7/2009 | Sternby |
| 2009/0173682 A1 | 7/2009 | Robinson |
| 2009/0182263 A1 | 7/2009 | Burbank |
| 2009/0187138 A1 | 7/2009 | Lundtveit |
| 2009/0216045 A1 | 8/2009 | Singh |
| 2009/0223539 A1 | 9/2009 | Gibbel |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0314063 A1 | 12/2009 | Sternby |
| 2010/0004588 A1 | 1/2010 | Yeh |
| 2010/0007838 A1 | 1/2010 | Fujimoto |
| 2010/0010027 A1 | 1/2010 | Chen et al. |
| 2010/0010429 A1 | 1/2010 | Childers |
| 2010/0022936 A1 | 1/2010 | Gura |
| 2010/0030151 A1 | 2/2010 | Kirsch |
| 2010/0042035 A1 | 2/2010 | Moissl |
| 2010/0051552 A1 | 3/2010 | Rohde |
| 2010/0078092 A1 | 4/2010 | Weilhoefer |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0100027 A1 | 4/2010 | Schilthuizen |
| 2010/0102190 A1 | 4/2010 | Zhu et al. |
| 2010/0106071 A1 | 4/2010 | Wallenberg |
| 2010/0114012 A1 | 5/2010 | Sandford |
| 2010/0130906 A1 | 5/2010 | Balschat |
| 2010/0137693 A1 | 6/2010 | Porras |
| 2010/0137782 A1 | 6/2010 | Jansson |
| 2010/0140149 A1 | 6/2010 | Fulkerson |
| 2010/0168546 A1 | 7/2010 | Kamath |
| 2010/0192686 A1 | 8/2010 | Kamen |
| 2010/0199670 A1 | 8/2010 | Robertson |
| 2010/0213127 A1 | 8/2010 | Castellarnau |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0252490 A1 | 10/2010 | Fulkerson |
| 2010/0274171 A1 | 10/2010 | Caleffi |
| 2010/0282662 A1 | 11/2010 | Lee |
| 2010/0312172 A1 | 12/2010 | Hoffman |
| 2010/0312174 A1 | 12/2010 | Hoffman |
| 2010/0326911 A1 | 12/2010 | Rosenbaum |
| 2010/0327586 A1 | 12/2010 | Mardirossian |
| 2011/0009798 A1 | 1/2011 | Kelly |
| 2011/0017665 A1 | 1/2011 | Updyke |
| 2011/0048949 A1 | 3/2011 | Ding et al. |
| 2011/0066043 A1 | 3/2011 | Banet |
| 2011/0071465 A1 | 3/2011 | Wang |
| 2011/0077574 A1 | 3/2011 | Sigg |
| 2011/0079558 A1 | 4/2011 | Raimann |
| 2011/0087187 A1 | 4/2011 | Beck |
| 2011/0100909 A1 | 5/2011 | Stange |
| 2011/0105983 A1 | 5/2011 | Kelly |
| 2011/0106003 A1 | 5/2011 | Childers |
| 2011/0120930 A1 | 5/2011 | Mishkin |
| 2011/0120946 A1 | 5/2011 | Levin |
| 2011/0130666 A1 | 6/2011 | Dong |
| 2011/0132838 A1 | 6/2011 | Curtis |
| 2011/0144570 A1 | 6/2011 | Childers |
| 2011/0160637 A1 | 6/2011 | Beiriger |
| 2011/0163030 A1 | 7/2011 | Weaver |
| 2011/0163034 A1 | 7/2011 | Castellarnau |
| 2011/0184340 A1 | 7/2011 | Tan |
| 2011/0189048 A1 | 8/2011 | Curtis |
| 2011/0220562 A1 | 9/2011 | Beiriger |
| 2011/0247973 A1 | 10/2011 | Sargand |
| 2011/0272337 A1 | 11/2011 | Palmer |
| 2011/0284377 A1 | 11/2011 | Rohde |
| 2011/0297593 A1 | 12/2011 | Kelly |
| 2011/0315611 A1 | 12/2011 | Fulkerson |
| 2011/0315632 A1 | 12/2011 | Freije |
| 2012/0006762 A1 | 1/2012 | McCabe |
| 2012/0016228 A1 | 1/2012 | Kroh |
| 2012/0031825 A1 | 2/2012 | Gura |
| 2012/0083729 A1 | 4/2012 | Childers |
| 2012/0085707 A1 | 4/2012 | Beiriger |
| 2012/0092025 A1 | 4/2012 | Volker |
| 2012/0115248 A1 | 5/2012 | Ansyln |
| 2012/0199205 A1 | 8/2012 | Eyrard |
| 2012/0220528 A1 | 8/2012 | VanAntwerp |
| 2012/0220926 A1 | 8/2012 | Soykan |
| 2012/0248017 A1 | 10/2012 | Beiriger |
| 2012/0258545 A1 | 10/2012 | Ash |
| 2012/0258546 A1 | 10/2012 | Marran |
| 2012/0259276 A1 | 10/2012 | Childers |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0302945 A1 | 11/2012 | Hedmann |
| 2013/0001165 A1 | 1/2013 | Pohlmeier |
| 2013/0015302 A1 | 1/2013 | Gkhan rter |
| 2013/0018301 A1 | 1/2013 | Weaver |
| 2013/0019994 A1 | 1/2013 | Schaer |
| 2013/0030356 A1 | 1/2013 | Ding |
| 2013/0037465 A1 | 2/2013 | Heyes |
| 2013/0062265 A1 | 3/2013 | Balschat |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228516 A1 | 9/2013 | Jonsson |
| 2013/0228517 A1 | 9/2013 | Roger |
| 2013/0231607 A1 | 9/2013 | Roger |
| 2013/0248426 A1 | 9/2013 | Pouchoulin |
| 2013/0256227 A1 | 10/2013 | Kelly |
| 2013/0274642 A1 | 10/2013 | Soykan |
| 2013/0304020 A1 | 11/2013 | Wilt |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0001112 A1 | 1/2014 | Karoor |
| 2014/0018727 A1 | 1/2014 | Burbank |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0190885 A1 | 7/2014 | Meyer |
| 2014/0190886 A1 | 7/2014 | Pudil |
| 2014/0190891 A1 | 7/2014 | Lura |
| 2014/0216250 A1 | 8/2014 | Meyer |
| 2014/0217020 A1 | 8/2014 | Meyer |
| 2014/0217027 A1 | 8/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2014/0224736 A1 | 8/2014 | Heide |
| 2014/0251908 A1 | 9/2014 | Ding |

(56) References Cited

U.S. PATENT DOCUMENTS

| | | |
|---|---|---|
| 2015/0057602 A1 | 2/2015 | Mason |
| 2015/0083647 A1 | 3/2015 | Meyer |
| 2015/0114891 A1 | 4/2015 | Meyer |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0258268 A1 | 9/2015 | Collier |
| 2015/0352270 A1 | 12/2015 | Pudil |
| 2016/0038666 A1 | 2/2016 | Kelly |
| 2016/0166748 A1 | 6/2016 | Meyer |
| 2016/0166751 A1 | 6/2016 | Meyer |
| 2016/0166752 A1 | 6/2016 | Meyer |
| 2016/0166753 A1 | 6/2016 | Meyer |
| 2017/0281847 A1 | 10/2017 | Venkatesh |

FOREIGN PATENT DOCUMENTS

| | | |
|---|---|---|
| CN | 102307650 | 1/2012 |
| CN | 202105667 | 1/2012 |
| CN | 101237918 | 1/2013 |
| CN | 101883584 | 7/2013 |
| CN | 103889481 A1 | 6/2014 |
| CN | 201510761050.6 | 8/2017 |
| DE | 3215003 | 4/1985 |
| DE | 102011052188 | 1/2013 |
| EP | 0022370 A1 | 1/1981 |
| EP | 0187109 | 7/1986 |
| EP | 266795 A2 | 11/1987 |
| EP | 0264695 | 4/1988 |
| EP | 0298587 | 6/1994 |
| EP | 0743071 | 11/1996 |
| EP | 1124599 | 5/2000 |
| EP | 1175238 | 11/2000 |
| EP | 711182 B1 | 6/2003 |
| EP | 2308526 | 10/2003 |
| EP | 1364666 A1 | 11/2003 |
| EP | 1523347 | 1/2004 |
| EP | 1523350 | 1/2004 |
| EP | 0906768 B1 | 2/2004 |
| EP | 1691863 | 4/2005 |
| EP | 2116269 | 2/2008 |
| EP | 1450879 | 10/2008 |
| EP | 1514562 | 4/2009 |
| EP | 2219703 | 5/2009 |
| EP | 1592494 B1 | 6/2009 |
| EP | 1490129 | 9/2009 |
| EP | 2100553 A1 | 9/2009 |
| EP | 2398529 | 11/2010 |
| EP | 2575827 A2 | 12/2010 |
| EP | 2100553 | 8/2011 |
| EP | 2388030 | 11/2011 |
| EP | 2576453 A2 | 12/2011 |
| EP | 2701580 | 11/2012 |
| EP | 2701595 | 11/2012 |
| EP | 1545652 B1 | 1/2013 |
| EP | 1345856 B1 | 3/2013 |
| EP | 2344220 B1 | 4/2013 |
| EP | 1351756 | 7/2013 |
| EP | 2190498 | 7/2013 |
| EP | 1414543 | 9/2013 |
| EP | 2701596 | 3/2014 |
| EP | 2740502 | 6/2014 |
| EP | 2883558 | 6/2015 |
| EP | 1787666 | 11/2015 |
| FR | 2237639 | 2/1977 |
| JP | 60-132606 | 7/1985 |
| JP | 60135064 | 7/1985 |
| JP | 08504116 | 5/1996 |
| JP | 2002306904 | 10/2002 |
| JP | 2006325668 A | 12/2006 |
| JP | 5099464 | 10/2012 |
| JP | 2013521862 | 6/2013 |
| WO | 9532010 A1 | 11/1995 |
| WO | 1996040313 | 12/1996 |
| WO | 9937342 | 7/1999 |
| WO | 9937342 A1 | 7/1999 |
| WO | 0057935 | 10/2000 |
| WO | WO2000057935 A1 | 10/2000 |
| WO | 200066197 A1 | 11/2000 |
| WO | 2000066197 | 11/2000 |
| WO | 200170307 A1 | 9/2001 |
| WO | 2001085295 A2 | 9/2001 |
| WO | 0185295 A2 | 11/2001 |
| WO | 2002043859 | 6/2002 |
| WO | 2003043677 A2 | 5/2003 |
| WO | 2003043680 | 5/2003 |
| WO | 2003051422 A2 | 6/2003 |
| WO | 2004008826 | 1/2004 |
| WO | 2004009156 | 1/2004 |
| WO | 2004030716 A2 | 4/2004 |
| WO | 2004030717 A2 | 4/2004 |
| WO | 2004064616 A2 | 8/2004 |
| WO | 2004062710 A3 | 10/2004 |
| WO | 2004105589 A2 | 12/2004 |
| WO | 2005044339 | 5/2005 |
| WO | 2004105589 A3 | 6/2005 |
| WO | 2005061026 | 7/2005 |
| WO | 2005123230 | 12/2005 |
| WO | 2005123230 A2 | 12/2005 |
| WO | 2006023589 | 3/2006 |
| WO | 2006124431 A2 | 11/2006 |
| WO | 2007010164 A2 | 1/2007 |
| WO | 2007089855 A2 | 8/2007 |
| WO | 2007146162 A2 | 12/2007 |
| WO | 2007146162 A3 | 12/2007 |
| WO | 2008037410 | 4/2008 |
| WO | 2008051994 | 5/2008 |
| WO | 2009026603 | 12/2008 |
| WO | 2009024566 | 2/2009 |
| WO | 2009026603 A1 | 3/2009 |
| WO | 2009061608 | 5/2009 |
| WO | 2009064984 | 5/2009 |
| WO | 2009067071 A1 | 5/2009 |
| WO | 2009071103 | 6/2009 |
| WO | WO 2009/073567 | 6/2009 |
| WO | 2009094184 | 7/2009 |
| WO | 2009132839 A1 | 11/2009 |
| WO | 2009157877 A1 | 12/2009 |
| WO | 2009157878 A1 | 12/2009 |
| WO | 20090157877 | 12/2009 |
| WO | 2010028860 | 3/2010 |
| WO | 2010028860 A1 | 3/2010 |
| WO | 2010042666 | 4/2010 |
| WO | 2010042666 A2 | 4/2010 |
| WO | 2010052705 A1 | 5/2010 |
| WO | 2010062698 | 6/2010 |
| WO | 2010096659 | 10/2010 |
| WO | 2010121820 | 10/2010 |
| WO | 2010102190 A4 | 11/2010 |
| WO | 2011017215 A1 | 2/2011 |
| WO | 2011025705 A1 | 3/2011 |
| WO | 2011072337 | 8/2011 |
| WO | 2011113572 A1 | 9/2011 |
| WO | WO 2011/112317 | 9/2011 |
| WO | 2012026978 | 3/2012 |
| WO | 2012042323 | 4/2012 |
| WO | 2012050781 | 4/2012 |
| WO | 2012051996 | 4/2012 |
| WO | 2012067585 | 5/2012 |
| WO | 2010042666 A3 | 6/2012 |
| WO | 2012138604 A2 | 10/2012 |
| WO | 2012148781 | 11/2012 |
| WO | 2012148786 | 11/2012 |
| WO | 2012148789 | 11/2012 |
| WO | 2012162515 A2 | 11/2012 |
| WO | 20120277551 | 11/2012 |
| WO | 2012172398 | 12/2012 |
| WO | 2013019179 A1 | 2/2013 |
| WO | 2013019994 A2 | 2/2013 |
| WO | 2013025844 | 2/2013 |
| WO | 2013025844 A2 | 2/2013 |
| WO | 2013027214 | 2/2013 |

(56) References Cited

FOREIGN PATENT DOCUMENTS

| WO | 2013028809 A2 | 2/2013 |
| WO | 2013028809 A3 | 2/2013 |
| WO | 2013019994 A3 | 4/2013 |
| WO | 2013025844 A3 | 5/2013 |
| WO | 2013103607 A1 | 7/2013 |
| WO | 2013103906 | 7/2013 |
| WO | 2013110906 | 8/2013 |
| WO | 2013110919 | 8/2013 |
| WO | 2013114063 A1 | 8/2013 |
| WO | 2013121162 A1 | 8/2013 |
| WO | 2013140346 | 9/2013 |
| WO | 2013141896 | 9/2013 |
| WO | 2013188861 A1 | 12/2013 |
| WO | 14066254 | 5/2014 |
| WO | 14066255 | 5/2014 |
| WO | 14077082 | 5/2014 |
| WO | WO 2014/099631 | 6/2014 |
| WO | 2014117000 | 7/2014 |
| WO | 2014121158 A1 | 8/2014 |
| WO | 2014121162 | 8/2014 |
| WO | 2014121163 | 8/2014 |
| WO | 2014121167 | 8/2014 |
| WO | 2014121169 | 8/2014 |
| WO | WO 2014/159918 | 10/2014 |
| WO | 2015071247 A1 | 5/2015 |
| WO | WO2017001358 | 1/2017 |

OTHER PUBLICATIONS

Extended European Search Report for App. No. 20160568.0, dated Jun. 17, 2020.
[NPL264] PCT/US2014/014357 International Search Report and Written Opinion dated May 19, 2014.
[NPL268] Ronco et al. 2008, Cardiorenal Syndrome, Journal American College Cardiology, 52:1527-1539, Abstract.
[NPL27] Overgaard. et. al., Relations between excitability and contractility in rate soleusmuscle: role of the Na+—K+ pump and Na+—K—S gradients. Journal of Physiology, 1999, 215-225, 518(1).
[NPL306] Coast, et al. 1990, An approach to Cardiac Arrhythmia analysis Using Hidden Markov Models, IEEE Transactions on Biomedical Engineering. 1990, 37(9):826-835.
[NPL309] Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
[NPL311] U.S. Appl. No. 13/424,479.
[NPL313] U.S. Appl. No. 13/424,525.
[NPL377] European Search Report 12819714.2-1651/2739325 PCT/US2012049398, dated Jun. 12, 2015.
[NPL378] PCT/US2014/14343 Intl Search Report & Written Opinion, dated May 9, 2014.
[NPL379] PCT/US2014/014350 International Search Report and Written Opinion dated May 2014.
[NPL380] EP 14746793 Supplementary European Search Report dated Aug. 18, 2016.
[NPL381] EP 14746791 Supplementary European Search Report dated Aug. 19, 2016.
[NPL382] EP 14746799 Supplementary European Seach Report dated Aug. 18, 2016.
[NPL386] The FHN Trial Group. In-Center. Hemodialysis Six Times per Week versus Three Times per Week, New England Journal of Medicine, 2010 Abstract.
[NPL39] PCT/US2012/034332, International Search Report, dated Jul. 5, 2012.
[NPL462] Office Action in U.S. Appl. No. 13/757,717 dated Dec. 26, 2014.
[NPL463] Office Action in U.S. Appl. No. 13/757,709 dated Jun. 6, 2015.
[NPL464] Office Action in U.S. Appl. No. 13/757,709 dated Jan. 7, 2016.
[NPL465] Office Action in U.S. Appl. No. 13/757,728 dated Jan. 8, 2016.
[NPL466] Office Action in U.S. Appl. No. 13/757,728 dated Aug. 12, 2016.
[NPL467] Office Action in U.S. Appl. No. 13/757,796 dated Apr. 13, 2015.
[NPL468] Office Action in U.S. Appl. No. 13/757,796 dated Dec. 21, 2015.
[NPL469] Office Action in U.S. Appl. No. 13/836,538 dated Aug. 19, 2015.
[NPL470] Office Action in U.S. Appl. No. 13/836,538 dated Jan. 11, 2016.
[NPL471] Office Action in U.S. Appl. No. 13/836,538 dated Apr. 27, 2016.
[NPL472] Office Action in U.S. Appl. No. 13/757,722 dated May 19, 2016.
[NPL473] Office Action in U.S. Appl. No. 13/757,709 dated Jan. 7, 2016.
[NPL474] Office Action in U.S. Appl. No. 13/757,693 dated Nov. 13, 2015.
[NPL475] Office Action in U.S. Appl. No. 13/757,693 dated May 23, 2016.
[NPL476] Office Action in U.S. Appl. No. 13/757,709 dated Jun. 6, 2015.
[NPL47] U.S. Appl. No. 61/480,544.
[NPL481] Office Action in U.S. Appl. No. 13/757,794 dated Oct. 21, 2015.
[NPL482] Office Action in U.S. Appl. No. 13/757,794 dated May 2, 2016.
[NPL483] Office Action in U.S. Appl. No. 13/424,525 dated Aug. 11, 2015.
[NPL484] Office Action in U.S. Appl. No. 13/424,525 dated Feb. 25, 2016.
[NPL485] Office Action in U.S. Appl. No. 13/424,525 dated Jun. 17, 2016.
[NPL486] Office Action in U.S. Appl. No. 13/424,525 dated Oct. 20, 2016.
[NPL487] Office Action in U.S. Appl. No. 13/424,479 dated Nov. 24, 2014.
[NPL488] Office Action in U.S. Appl. No. 14/566,686 dated Apr. 28, 2016.
[NPL489] Office Action in U.S. Appl. No. 13/424,533 dated Oct. 22, 2013.
[NPL490] Office Action in U.S. Appl. No. 13/424,533 dated Apr. 18, 2014.
[NPL491] Office Action in U.S. Appl. No. 13/424,533 dated Jan. 5, 2015.
[NPL492] Office Action in U.S. Appl. No. 13/424,533 dated Jun. 2, 2015.
[NPL493] Office Action in U.S. Appl. No. 13/424,533 dated Jul. 14, 2016.
[NPL496] Welgemoed, T.J., Capacitive Deionization Technology: An Alternative to desalination Solution, Desalination 183 (2005) 327-340.
[NPL497] European Search Report for App. No. 15193645.7, dated Apr. 15, 2016.
[NPL498] European Search Report in App. No. 15193720.8 dated Apr. 26, 2016.
[NPL499] EP. App. 14746193.3 Search Report dated Oct. 19, 2016.
[NPL528] Office Action in U.S. Appl. No. 14/555,393 dated May 4, 2016.
[NPL529] Office Action in U.S. Appl. No. 14/555,393 dated Nov. 1, 2016.
[NPL530] Office Action in U.S. Appl. No. 14/555,414 dated May 4, 2016.
[NPL531] Office Action in U.S. Appl. No. 14/555,414 dated Nov. 3, 2016.
[NPL534] Office Action in U.S. Appl. No. 13/586,824 dated Dec. 21, 2015.
[NPL535] Office Action in U.S. Appl. No. 13/586,824 dated Jun. 4, 2016.
[NPL546] Office Action in Chinese Application No. 201480007138.2 dated Sep. 28, 2016.

(56) References Cited

OTHER PUBLICATIONS

[NPL553] Ruperez et al., Comparison of a tubular pulsatile pump and a volumetric pump for continuous venovenous renal replacement therapy in a pediatric animal model, 51 ASAIO J. 372, 372-375 (2005).
[NPL554] St. Peter et al., Liver and kidney preservation by perfusion, 359 The Lancet 604, 606(2002).
[NPL555] Dasselaar et al., Measurement of relative blood volume changes during hemodialysis: merits and limitations, 20 Nephrol Dial Transpl. 2043, 2043-2044 (2005).
[NPL556] Ralph T. Yang, Adsorbents: Fundamentals and Applications 109 (2003).
[NPL557] Henny H. Billett, Hemoglobin and Hematocrit, in Clinical Methods: The History, Physical, and Laboratory Examinations 719(HK Walker, WD Hall, & JW Hurst ed., 1990).
[NPL558] Office Action in U.S. Appl. No. 13/565,733 dated Jan. 11, 2016.
[NPL559] Office Action in U.S. Appl. No. 13/565,733 dated Jun. 11, 2015.
[NPL55] U.S. Appl. No. 13/424,454.
[NPL560] Office Action in U.S. Appl. No. 13/586,824 dated Jun. 4, 2015.
[NPL562] Office Action in U.S. Appl. No. 13/757,796 dated Apr. 13, 2015.
[NPL563] Office Action in U.S. Appl. No. 13/757,796 dated Dec. 21, 2015.
[NPL564] Office Action in U.S. Appl. No. 13/835,735 dated Oct. 13, 2015.
[NPL565] Office Action in U.S. Appl. No. 13/836,079 dated Apr. 17, 2015.
[NPL566] Office Action in U.S. Appl. No. 13/836,079 dated Jun. 30, 2016.
[NPL569] Office Action in U.S. Appl. No. 13/791,755 dated Mar. 16, 2016.
[NPL570] Office Action in U.S. Appl. No. 13/791,755 dated Aug. 9, 2016.
[NPL571] Office Action in U.S. Appl. No. 13/835,735 dated Jun. 16, 2016.
[NPL572] Office Action in U.S. Appl. No. 13/836,079 dated Nov. 6, 2015.
[NPL578] Office Action in U.S. Appl. No. 13/791,755 dated Sep. 10, 2015.
[NPL579] Office Action in U.S. Appl. No. 13/791,755 dated Apr. 20, 2015.
[NPL57] U.S. Appl. No. 13/424,467.
[NPL580] Office Action in U.S. Appl. No. 14/259,589 dated Nov. 4, 2016.
[NPL581] Office Action in U.S. Appl. No. 14/261,651 dated Aug. 25, 2016.
[NPL586] International Search Report from International Application No. PCT/US2014/014347 dated May 9, 2014.
[NPL587] International Search Report for PCT/US2015/060090 date of completion is Feb. 9, 2016 (3 pages).
[NPL592] St. Peter et al., Liver and Kidney Preservation by perfusion, 369 The Lancet 604, 606 (2002).
[NPL593] Office Action for Chinese Application 20148007136.3, dated Jun. 2, 2016.
[NPL593] Office Action in Chinese Application No. 20148007136.3 dated Jun. 15, 2017.
[NPL594] Office Action for Chinese Application 20148007136.3, dated Jan. 26, 2017.
[NPL597] Franks, Gene, Cabon Filtration: What it does, What it doesnt, Mar. 14, 2012, pp. 1-3.
[NPL597] Franks, Gene, Carbon Filtration: What it does, What it doesnt, Mar. 14, 2012, pp. 1-3.
[NPL598] PCT/US2014/014352 International Search Report and Written Opinion dated Jul. 7, 2014.
[NPL599] PCT/US2014/014352 International Prelminary Report on Patentability, dated Aug. 14, 2015.

[NPL600] Hamm et al,. Sorbent regenerative hemodialysis as a potential cuase of acute hypercapnia, Kidney International, vol. 21, (1982), pp. 416-418.
[NPL624] Office Action in Chinese Application No. 201480007132.5 dated Jul. 19, 2017.
[NPL627] EP Search Report for Application No. 16204175.0 dated Mar. 29, 2017.
[NPL629] Office Action for Chinese Application 201510713880.1 dated Apr. 1, 2017.
[NPL629] Office Action in Chinese Application 201510713880.1 dated Apr. 1, 2017.
[NPL62] U.S. Appl. No. 13/424,533.
[NPL631] Understanding Dialysate Bicarbonate—A simple approach to understanding a complex equation by Fresenius Medical Care, 2011.
[NPL635] International Search Report, Application PCT/US2016/043948, dated Feb. 2, 2017.
[NPL636] Written Opinion, Application PCT/2016/043948, dated Feb. 2, 2017.
[NPL637] International Search Report, Application PCT/US2016/043935, dated Feb. 2, 2017.
[NPL638] Written Opinion, Application PCT/US2016/043935, dated Feb. 2, 2017.
2017-530641_OA.
[NPL105] Brynda, et. al., The detection of toman 2-microglcbuiin by grating coupler immunosensor with three dimensional antibody networks. Biosensors & Bioelectronics, 1999, 363-368, 14(4).
[NPL10] Wheaton, et al., DOWEX Ion Exchange Resins— Fundamentals of Ion Exchange; Jun. 2000, pp. 1-9. http://www.dow.com/scripts/litorder.asp?filepath=liquidseps/pdfs/noreg/177-01837.pdf.
[NPL111] Zhong, et. al., Miniature urea sensor based on H(+)-ion sensitive field effect transistor and its application in clinical analysis, Chin. J. Biotechnol., 1992, 57-65. 8(1).
[NPL119] PCT/US2012/034331, International Search Report and Written Opinion dated Jul. 9, 2012.
[NPL121] Roberts M, The regenerative dialysis (REDY) sorbent system. Nephrology, 1998, 275-278:4.
[NPL138] U.S. Appl. No. 61/480,544.
[NPL139] U.S. Appl. No. 61/480,541 dated Apr. 29, 2011.
[NPL142] Hemametrics, Crit-Line Hematocrit Accuracy, 2003, 1-5, vol. 1, Tech Note No. 11 (Rev. D).
[NPL144] Weissman, S., et al., Hydroxyurea-induced hepatitis in human immunodeficiency virus-positive patients. Clin. Infec. Dis, (Jul. 29, 1999): 223-224.
[NPL146] PCT/US2012/034334, International Search Report, dated Jul. 6, 2012.
[NPL147] PCT/US2012/034335, International Search Report, dated Sep. 5, 2012.
[NPL148] PCT/US/2012/034327, International Search Report, dated Aug. 13, 2013.
[NPL149] PCT/US/2012/034329, International Search Report, dated Dec. 3, 2012.
[NPL161] EP13182115.9-1651 European Search Report, dated Feb. 3, 2014.
[NPL162] International Search Report from PCT/US2012/051946 dated Mar. 4, 2013.
[NPL163] U.S. Appl. No. 61/526,209.
[NPL164] Written Opinion of the International Searching Authority for PCT/US2012/049398 dated Feb. 25, 2013.
[NPL169] Wang, Fundamentals of intrathoracic impedance monitoring in heart failure, Am. J. Cardiology, 2007, 3G-10G: Suppl.
[NPL16] PCT/US2014/067650 International Search Report Written Opinion dated Mar. 9, 2015.
[NPL170] Bleyer, et al, Kidney International. Jun. 2006; 69(12):2268-2273.
[NPL172] U.S. Appl. No. 29/446,285, filed Feb. 1, 2013.
[NPL175] Marchant, et. al., In vivo Biocompatibility Studies 1: The Cage Implant System and a Biodegradable Hydrogel, J. Biomed. Mat. Res., 1983, 301-325: 17.
[NPL176] Bleyer, et. al., Sudden and cardiac death rated in hemodialysis patients, Kidney International. 1999, 1553-1559: 55.

(56) References Cited

OTHER PUBLICATIONS

[NPL178] PCT/US2012/025711, International Search Report dated Jul. 4, 2012.
[NPL179] PCT/US2013/020404, International Search Report, dated Jan. 4, 2013.
[NPL187] PCT/US2012/034333, International Preliminary Report on Patentability, dated Oct. 29, 2013.
[NPL188] PCT/US2012/034333, International Search Report, dated Aug. 29, 2012.
[NPL188] PCT/US2012/034333, International Search Report, dated Aug. 29, 2013.
[NPL189] PCT/US2012/051011, International Search Report, dated Jan. 17, 2014.
[NPL197] PCT/US2012/034330, International Preliminary Report on Patentability, dated Oct. 29, 2013.
[NPL205] Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
[NPL217] U.S. Appl. No. 13/757,722, filed Feb. 1, 2013.
[NPL218] U.S. Appl. No. 13/757,794, filed Feb. 2, 2012.
[NPL219] U.S. Appl. No. 13/791,755, filed Mar. 8, 2013.
[NPL21] U.S. Appl. No. 13/424,479 dated Nov. 1, 2012.
[NPL220] U.S. Appl. No. 13/757,792, filed Feb. 2, 2013.
[NPL222] U.S. Appl. No. 13/757,794, filed Feb. 2, 2013.
[NPL227] U.S. Appl. No. 13/837,287, filed Mar. 15, 2013.
[NPL22] U.S. Appl. No. 13/424,429 dated Nov. 1, 2012.
[NPL230] Redfield, et. al, Restoration of renal response to atria! natriuretic factor in experimental low-output heat failure, Am. J. Physiol., Oct. 1, 1989, R917-923:257.
[NPL231] Rogoza, et. al., Validation of A&D UA-767 device for the self-measurement of blood pressure, Blood Pressure Monitoring, 2000, 227-231, 5(4).
[NPL234] Lima, et. al., An electrochemical sensor based on nanostructure hollsndite-type manganese oxide for detection of potassium ion, Sensors, Aug. 24, 2009, 6613-8625, 9.
[NPL235] Maclean, et, al., Effects of hindlimb contraction on pressor and muscle interstitial metabolite responses in the cat, J. App. Physiol., 1998, 1583-1592, 85(4).
[NPL237] U.S. Appl. No. 13/757,693, dated Feb. 1, 2013.
[NPL238] PCT Application, PCT/US20013/020404, filed Jan. 4, 2013.
[NPL23] U.S. Appl. No. 13/424,525.
[NPL240] U.S. Appl. No. 13/836,973, filed Mar. 15, 2013.
[NPL241] U.S. Appl. No. 14/259,655, filed Apr. 23, 2014.
[NPL242] U.S. Appl. No. 14/259,589, filed Apr. 23, 2014.
[NPL243] U.S. Appl. No. 13/757,693, filed Jan. 4, 2013.
[NPL244] U.S. Appl. No. 13/836,079, filed Mar. 15, 2013.
[NPL245] U.S. Appl. No. 14/240,129, filed Aug. 22, 2013.
[NPL246] PCT/US2014/014346 International Search Report and Written Opinion.
[NPL247] U.S. Appl. No. 13/835,735, filed Mar. 15, 2013.
[NPL248] PCT/US2014/014345 International Search Report and Written Opinion, dated May 2014.
[NPL250] U.S. Appl. No. 13/835,735 IDS, filed Jun. 13, 2013.
[NPL26] Overgaard, et. al., Activity-induced recovery of excitability in K+-depressed rat soleus muscle, Am. J. P 280: R48-R55, Jan. 1, 2001.
[NPL310] U.S. Appl. No. 61/480,532.
[NPL312] U.S. Appl. No. 13/424,429 dated Nov. 1, 2012.
[NPL317] U.S. Appl. No. 61/480,530.
[NPL318] U.S. Appl. No. 61/480,528 dated Apr. 29, 2011.
[NPL32] Secemsky, et. al, High prevalence of cardiac autonomic dysfunction and T-wave alternans in dialysis patients. Heart Rhythm, Apr. 2011, 592-598: vol. 8, No. 4.
[NPL35] Wei, et. al., Fullerene-cryptand coated piezoelectric crystal urea sensor based on urease, Analytica Chimica Acta, 2001,77-85:437.
[NPL376] Gambro AK 96 Dialysis Machine Operators Manual, Dec. 2012. p. 1-140.
[NPL376] Gambro AK 96 Dialysis Machine Operators Manual, Dec. 2012. p. 141-280.
[NPL376] Gambro AK 96 Dialysis Machine Operators Manual, Dec. 2012. p. 281-420.
[NPL376] Gambro AK 96 Dialysis Machine Operators Manual, Dec. 2012. p. 421-534.
[NPL37] U.S. Appl. No. 13/368,225 dated Feb. 7, 2012.
[NPL383] Leifer et al., A Study on the Temperature Variation of Rise Velocity for Large Clean Bubbles, J. Atmospheric & Oceanic Tech., vol. 17, pp. 1392-1402, Oct. 2000.
[NPL384] Talaia, Terminal Velocity of a Bubble Rise in a Liquid Column, World Acad. of Sci., Engineering & Tech., vol. 28, pp. 264-268, Published Jan. 1, 2007.
[NPL46] Siegenthaler, et al., Pulmonary fluid status monitoring with intrathoracic impedance, Journal of Clinical Monitoring and Computing, 24:449-451, published Jan. 12, 2011.
[NPL561] Office Action in U.S. Appl. No. 13/757,792 dated Jun. 2, 2016.
[NPL639] International Search Report and Written Opinion in App. No. PCT/US2012/049398 dated Feb. 25, 2013.
[NPL640] Office Action in European App. No. 12819714.2 dated Aug. 5, 2016.
[NPL641] PCT/US2014/014343 Written Opinion dated Jan. 2, 2015.
[NPL642] PCT/US2014/014343 International Preliminary Search Report dated Mar. 18, 2015.
[NPL643] European Search Report for EP Appl. No. 1474679.4 dated Aug. 19, 2016.
[NPL644] Office Action for Chinese Application 201510761050.6 dated Aug. 2, 2017.
[NPL645] PCT/US2014/014355 International Search Report and Written Opinion dated May 1, 2014.
[NPL646] PCT/US2014/014355 International Preliminary Report dated Apr. 13, 2015.
[NPL647] EP 14746817.7 European Search Report dated Sep. 27, 2016.
[NPL650] Office Action in Chinese Application No. 201480007132.5 dated Feb. 27, 2017.
[NPL652] Office Action in Chinese Application No. 201280047921.2 dated Jun. 11, 2015.
[NPL654] International Preliminary Report from International Application No. PCT/US2014/014348 dated Jan. 9, 2015.
[NPL655] European Search Report from European Application No. EP 14746193.3 dated Oct. 19, 2016.
[NPL656] European Search Report from European Application No. EP 14746193.3 dated Jun. 8, 2016.
[NPL661] PCT/US2014/014346 Writtent Opinion dated Apr. 10, 2015.
[NPL662] PCT/US2014/014346 International Search Report and Writtent Opinion dated May 23, 2014.
[NPL663] EP 14746415.0 European Search Report dated Aug. 22, 2016.
[NPL664] Office Action in European Application No. EP 14746415.0 dated Apr. 19, 2017.
[NPL665] PCT/US2014/014357 International Search Report and Written Opinion dated May 19, 2014.
[NPL666] PCT/US2014/014357 Written Opinion dated Feb. 18, 2015.
[NPL667] European Search Report in European Application No. EP 14746010.9 dated Sep. 15, 2016.
[NPL670] Office Action in European Application No. 14746415.0 dated Apr. 19, 2017.
[NPL67] U.S. Appl. No. 13/424,490.
[NPL68] U.S. Appl. No. 13/424,517.
[NPL704] Written Opinion for PCT/US2015/060090 dated Feb. 16, 2016.
[NPL705] EP 13733819 Supplementary European Search Report dated Jan. 28, 2015.
[NPL713] EP Search Report and Opinion for Application No. 15193720.8 dated May 2, 2016.
[NPL714] Office action for European Application No. 15193720.8 dated Apr. 25, 2017.

(56) References Cited

OTHER PUBLICATIONS

[NPL723] PCT/US2012/051011, International Search Report and Written Opinion, dated Mar. 4, 2013.
[NPL724] Office Action for European Application No. 14746611.4 dated Jan. 3, 2017.
[NPL725] Supplemental Search Report and Search Opinion for European Application No. 14746611.4 dated Aug. 18, 2016.
[NPL728] Examination Report in Australian Application No. AU2014212135 dated May 25, 2017.
[NPL729] Office Action in Chinese Application No. 201480007138.2 dated May 31, 2017.
[NPL736] Office Action in European Application No. 14746193.3 dated Apr. 19, 2017.
[NPL739] European Office Action in Application No. 14746793.0 dated Apr. 13, 2017.
[NPL743] Examination report in Australian Application No. 2014212141 dated May 26, 2017.
[NPL744] Examination report for Australian Application 2015361083 dated Jul. 20, 2017.
[NPL750] European Search Report and Search Opinion for European Application EP15193720 dated May 2, 2016.
[NPL751] Office Action in European Application No. 15193720.8 dated Apr. 25, 2017.
[NPL752] International Preliminary Report on Patentability for PCT2015/060090 dated Jun. 13, 2017.
[NPL753] European Search Report for European Application EP 15193830.5 dated May 4, 2016.
[NPL754] Office Action for European Application No. 15193645.7 dated Apr. 21, 2017.
[NPL81] U.S. Appl. No. 61/480,539 dated Apr. 29, 2011.
[NPL84] U.S. Appl. No. 61/480,535 dated Apr. 29, 2011.
[NPL90] Nedelkov, et. al., Design of buffer exchange surfaces and sensor chips for biosensor chip mass spectrometry, Proteomics, 2002, 441-446, 2(4).
PCT/US2017/025868 International Search Report dated Jun. 29, 2017.
PCT/US2017/025868 Written Opinion dated Jun. 29, 2017.
PCTUS2017025858 International Search Report dated Jun. 29, 2017.
PCTUS2017025858 Written Opinion dated Jun. 29, 2017.
PCTUS2017025876 International Search Report dated Jun. 29, 2017.
PCTUS2017025876 Written Opinion dated Jun. 29, 2017.
Office Action in European App. No. 19158804.5, dated Sep. 4, 2020.

\* cited by examiner

PNEUMATIC MANIFOLD FOR A DIALYSIS SYSTEM

CROSS-REFERENCE TO RELATED APPLICATION

This application claims the benefit of and priority to U.S. Provisional Patent Application No. 62/595,859 filed Dec. 7, 2017, the entire disclosure of which is incorporated by reference herein.

FIELD OF THE INVENTION

The invention relates to a pneumatic manifold for controlling a fluid level in an arterial and/or venous drip chamber of a dialysis system. The pneumatic manifold includes pneumatic valves fluidly connected to conduits and one or more pumps. Selectively activating the pneumatic valves can result in pressure changes for raising or lowering a fluid level in the arterial and/or venous drip chambers.

BACKGROUND

Venous and arterial drip chambers are sometimes used by known systems and methods to separate entrained air bubbles from blood before blood enters a dialyzer or is returned to a patient. The effective removal of air bubbles usually requires specific fluid levels in the drip chambers. However, known systems oftentimes fail to provide for control of fluid levels. Moreover, a required fluid level can depend on a flow rate of the blood, which can be changed during a dialysis session, and may not be monitored or controlled by known systems and methods. Changes in pressure in an extracorporeal circuit can also cause fluid levels in the drip chambers to raise or lower wherein the fluid levels in the drip chambers must be actively raised or lowered in response to changes in the blood flow rate as well as changes in the fluid pressure in the extracorporeal circuit. However, known systems and methods do not 1) actively control fluid levels or 2) effectively control such fluid levels.

Hence, there is a need for systems and related methods that can effectively raise or lower the fluid levels in each of the drip chambers. To increase manufacturability and reduce costs, there is a further need for the systems and methods to use a single manifold containing valves and a pump capable of controlling the fluid level in both the arterial and venous drip chamber, rather than one or more separate sets of tubing and valves.

SUMMARY OF THE INVENTION

The first aspect of the invention relates to a pneumatic manifold. In any embodiment, the pneumatic manifold can comprise an internal conduit; a first fluid line fluidly connected to the internal conduit; the first fluid line fluidly connectable to a venous drip chamber in an extracorporeal circuit of a dialysis system; a second fluid line fluidly connected to the internal conduit; the second fluid line fluidly connectable to an arterial drip chamber in an extracorporeal circuit of a dialysis system; a venous valve fluidly connecting the first fluid line to the internal conduit; an arterial valve fluidly connecting the second fluid line to the internal conduit; a negative valve fluidly connecting the internal conduit to an outlet; a positive valve fluidly connecting the internal conduit to an inlet; the inlet and outlet fluidly connectable by a third fluid line containing a pump; and a controller selectively activating or deactivating the venous valve, arterial valve, positive valve, and negative valve; the controller controlling a fluid level in the venous drip chamber and arterial drip chamber by activating or deactivating the valves.

In any embodiment, the pneumatic manifold can comprise a line clamp valve; the line clamp valve fluidly connecting the internal conduit and a second outlet; the second outlet fluidly connectable to a line clamp in the extracorporeal circuit.

In any embodiment, the pneumatic manifold can comprise a vent fluidly connected to the positive valve.

In any embodiment, the pneumatic manifold can comprise a vent fluidly connected to the line clamp valve.

In any embodiment, the pneumatic manifold can comprise a line clamp check valve positioned between the positive valve and the line clamp valve; the line clamp check valve allowing fluid to move only in a direction from the positive valve to the line clamp valve.

In any embodiment, the pneumatic manifold can comprise a first flow restrictor positioned between the venous valve and the first fluid line; and a second flow restrictor positioned between the arterial valve and the second fluid line.

In any embodiment, the pneumatic manifold can comprise a venous pressure sensor positioned between the venous valve and the first fluid line; and an arterial pressure sensor positioned between the arterial valve and the second fluid line.

In any embodiment, the pneumatic manifold can comprise a pressure sensor positioned in the internal conduit.

In any embodiment, the pneumatic manifold can comprise a line clamp filter; the line clamp filter fluidly connected to the negative valve and a second inlet of the pneumatic manifold; wherein the internal conduit is fluidly connected to the outlet when the negative valve is activated and fluidly connected to the line clamp filter when the negative valve is deactivated.

In any embodiment, the pneumatic manifold can comprise a vent fluidly connected to the line clamp valve; wherein the internal conduit is fluidly connected to the second outlet when the line clamp valve is activated and fluidly connected to the vent when the line clamp valve is deactivated.

The features disclosed as being part of the first aspect of the invention can be in the first aspect of the invention, either alone or in combination.

The second aspect of the invention relates to a method of controlling a fluid level in an arterial drip chamber and/or venous drip chamber. In any embodiment, the method can comprise selectively activating or deactivating one or more valves in the pneumatic manifold of the first aspect of the invention.

In any embodiment, the step of controlling the fluid level in the arterial drip chamber can comprise the step of raising the fluid level in the arterial drip chamber by selectively activating the negative valve and the arterial valve.

In any embodiment, the step of controlling the fluid level in the arterial drip chamber can comprise the step of lowering the fluid level in the arterial drip chamber by selectively activating the positive valve and the arterial valve.

In any embodiment, the step of controlling the fluid level in the venous drip chamber can comprise the step of raising the fluid level in the venous drip chamber by selectively activating the negative valve and the venous valve.

In any embodiment, the step of controlling the fluid level in the venous drip chamber can comprise the step of lowering the fluid level in the venous drip chamber by selectively activating the positive valve and the venous valve.

In any embodiment, the method can comprise the step of stopping blood flow in a venous line of the extracorporeal circuit by selectively activating the positive valve and a line clamp valve in the pneumatic manifold; the line clamp valve fluidly connecting the internal conduit and a second outlet; the second outlet fluidly connected to a venous line clamp.

In any embodiment, the step of stopping blood flow in the venous line of the extracorporeal circuit can be performed in response to air detected in the venous line.

In any embodiment, the step of controlling the fluid level in the venous drip chamber can comprise first opening the venous line clamp and then activating the venous valve and either the positive valve or negative valve.

In any embodiment, the step of controlling the fluid level in the arterial drip chamber can comprise first opening the venous line clamp and then activating the arterial valve and either the positive valve or negative valve.

In any embodiment, the controller can be programmed to maintain a set fluid level in the arterial drip chamber and/or venous drip chamber by selectively activating the one or more valves.

In any embodiment, the method can comprise the steps of monitoring a pressure in the pneumatic manifold in the first fluid line, the second fluid line, or both; and generating an alarm indicating an occlusion if a pressure in the first fluid line, the second fluid line, or both does not show a pulsatile response.

The features disclosed as being part of the second aspect of the invention can be in the second aspect of the invention, either alone or in combination.

DETAILED DESCRIPTION OF THE INVENTION

Figure 1:
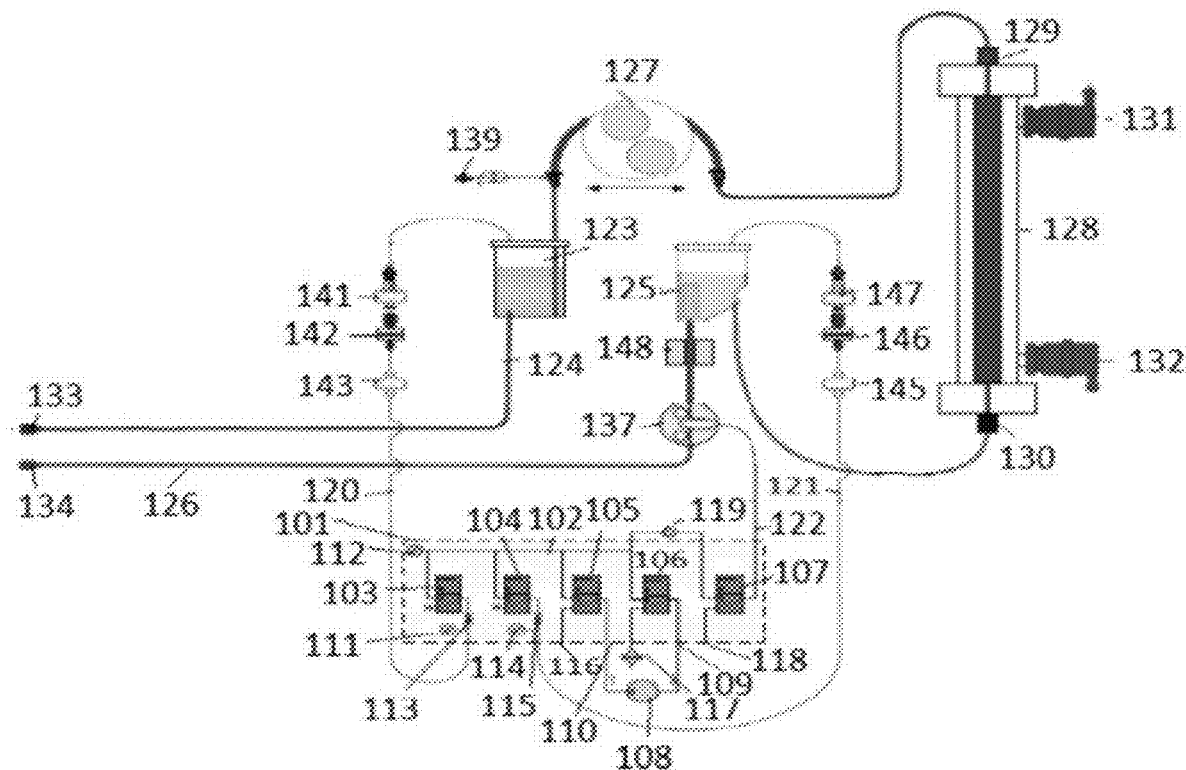
FIG. 1 is a schematic of an extracorporeal circuit including a pneumatic manifold.

Unless defined otherwise, all technical and scientific terms used generally have the same meaning as commonly understood by one of ordinary skill in the art.

The articles "a" and "an" are used to refer to one or to over one (i.e., to at least one) of the grammatical object of the article. For example, "an element" means one element or over one element.

"Activating" or "activated" can refer to connecting or providing power to flow or be electrically conveyed to any component. One non-limiting example can be a valve that can require electrical power to stay in either a closed or an open state.

The terms "allowing fluid to move only in a direction" or to "allow fluid to move only in a direction" can refer to preventing fluid movement through a fluid line or conduit in a first direction while permitting fluid movement through the fluid line or conduit in a second direction.

The terms "air detected" or to "detect air" can refer to making a determination that air, an air bubble, or combinations thereof being present in a liquid or fluid.

An "arterial drip chamber" can refer to a device that separates and captures air mixed with blood. In one non-limiting example, the arterial drip chamber can be placed in an arterial line of an extracorporeal flow path.

An "arterial pressure sensor" can be a pressure sensor positioned to measure the pressure of gas in a fluid line. The pressure to be measured can be between an arterial valve and an arterial drip chamber.

The term "arterial valve" can refer to a pneumatic valve controlling air movement to and from an arterial drip chamber.

The term "comprising" includes, but is not limited to, whatever follows the word "comprising." Use of the term indicates the listed elements are required or mandatory but that other elements are optional and may be present.

The term "consisting of" includes and is limited to whatever follows the phrase "consisting of" The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

A "controller" can refer to a device which monitors and affects the operational conditions of a given system. The operational conditions are typically referred to as output variables of the system wherein the output variables can be affected by adjusting certain input variables.

The terms "control," "controlling," or "controls" can refer to the ability of one component to direct the actions of a second component.

"Deactivating" or "deactivated" can refer to disconnecting or preventing power from flowing or being electrically conveyed to any component. One non-limiting example can be a valve that can require electrical power to stay in either a closed or an open state.

The term "dialysis system" can refer to a set of components configured to carry out dialysis therapy of any type including peritoneal dialysis, hemodialysis, hemofiltration, hemodiafiltration, or ultrafiltration.

An "extracorporeal circuit" can refer to a path through which blood or fluid will travel during dialysis.

A "flow restrictor" can refer to an element or grouping of elements that resist the flow of fluid through the element or grouping of elements such that the fluid pressure within a flow stream that passes through the element or grouping of elements is greater upstream of the element or grouping of elements than downstream of the element or grouping of elements. A flow restrictor may be an active or passive device. Non-limiting examples of passive flow restriction devices are orifices, venturis, spray nozzles, a narrowing, or a simple length of tubing with flow cross section that produces the desired pressure drop when the fluid flows through the flow restrictor, such tubing being essentially rigid or compliant. Non-limiting examples of active flow restrictors are pinch valves, gate valves and variable orifice valves.

The term "fluid level" can refer to a height of a fluid within a component. For example, the component can be an arterial or venous drip chamber.

A "fluid line" can refer to a tubing or conduit through which a fluid or fluid containing gas can pass. The fluid line can also contain air during different modes of operation such as cleaning or purging of a line.

The term "fluidly connectable," "fluidly connect," "for fluid connection," and the like, can refer to the ability of providing for the passage of fluid, gas, or a combination thereof, from one point to another point. The two points can be within or between any one or more of compartments, modules, systems, components, and rechargers, all of any type. The connection can optionally be disconnected and then reconnected. The term "fluidly connected" refers to a state of fluid connection, which can be distinguished from the described term of "fluid connectable," which refers to the ability of providing for the passage of fluid, gas, or a combination thereof, and not the state of fluid connection, in fact.

The term "generating an alarm" or to "generate an alarm" can refer to generating or signaling to a user a state or condition of a system.

The term "inlet" can refer to a portion of a component through which air can be drawn into the component through a fluid line. In one non-limiting example, the component can be a manifold.

An "internal conduit" can refer to a fluid pathway partially or entirely inside a manifold.

A "line clamp" can refer to a component that can obstruct or otherwise impede fluid flow through a fluid line.

A "line clamp check valve" can refer to a valve that only allows fluid movement through a fluid line in a single direction.

A "line clamp filter" can refer to an air filter that removes particulate matter of any size or shape from air, fluid, or combinations thereof.

A "line clamp valve" can refer to a valve that controls air movement to and from a line clamp. One non-limiting type of valve can be a pneumatic valve.

The term "lowering the fluid level" or to "lower the fluid level" can refer to a decrease in a height or level of a fluid in a chamber or component of any type.

The term "maintain a set fluid level" means to keep a fluid level in a chamber or component at a specific height, or within a specific height range.

The term "monitoring" or to "monitor" refers to determining a state of a system or variable.

The term "negative valve" can refer to a valve in a component that allows a pump to cause a pressure decrease in an internal conduit of a component when activated. In one non-limiting example, the component can be a pneumatic manifold.

An "occlusion" can be a blockage, either partial or full, of a component, conduit, or flow passage of any type.

The terms "opening" or to "open" a line clamp can refer to causing a line clamp to allow fluid or air movement through a fluid line.

The term "outlet" refers to a portion of a component through which fluid or air can be pulled out of the component in a fluid line, conduit, or fluid passageway of any type. In one non-limiting embodiment, the component can be a manifold.

The term "perform" refers to one or more actions that a component, processer, algorithm, or method carries out. The actions can be set by instructions implemented by a component, processer, algorithm, or method of any type.

A "pneumatic manifold" can refer to a component containing one or more fluid pathways that uses air pressure to control one or more components. The pneumatic manifold can be used as part of a dialysis system.

The term "positive valve" can refer to a valve that allows a component to cause an increase in pressure in another component. In one non-limiting example, a positive valve can refer to a valve that allows a pump to increase pressure in an internal conduit of a manifold.

The term "pressure" refers to a force exerted by a gas on the walls of a component, container, or conduit.

The term "pressure sensor" can refer to a device or any suitable component for measuring the pressure of a gas or fluid in a vessel, container, or fluid line.

The term "programmed," when referring to a controller, can mean a series of instructions that cause a controller to perform certain steps.

The term "pulsatile response" refers to a change in pressure that rhythmically increases and decreases.

The term "pump" can refers to any device that causes the movement of fluids, gases, or combinations thereof, by applying force of any type including suction or pressure.

The terms "raising the fluid level" or to "raise the fluid level" can refer to increasing a height of a fluid in a chamber or component of any type.

The term "selectively activating or deactivating" can refer to providing power, e.g., electrical power, to one or more components. The selective activating or deactivating can lead to a set of components in an activated state and another set of components in a deactivated state to result in a discriminate activated configuration. In one non-limiting example, the components can be valves activated into a closed or open state. Alternatively, the valves can be deactivated into a closed or open state. In one non-limiting example of a discriminate activated configuration based on "selectively activating or deactivating" one or more valve, a fluid, gas, or combinations thereof, can be directed to a specific flow path based on the activated and deactivated state of the valves.

The term "stopping blood flow" or to "stop blood flow" can refer to preventing blood from moving through a fluid flow path.

A "venous drip chamber" can refer to a device that separates and captures air mixed with blood. In one non-limiting example, the venous drip chamber can be placed in a venous line of an extracorporeal flow path.

A "venous pressure sensor" can refer to a pressure sensor positioned to measure the pressure of gas in a fluid line. In one non-limiting example, the pressure of the gas to be measured can be between a venous valve and a venous drip chamber.

The term "venous valve" refers to a pneumatic valve controlling air movement to and from a venous drip chamber.

A "vent" can be an opening in a component through which air can escape the component. In one non-limiting embodiment, the vent can be in fluid connection with a fluid line in a manifold.

Pneumatic Manifold

FIG. 1 is a schematic representation of a pneumatic manifold 101 for use with a dialysis system. The pneumatic manifold 101 can control a fluid level in both an arterial drip chamber 123 connected to an arterial line 124 of an extracorporeal circuit, and a venous drip chamber 125 connected to a venous line 126 of the extracorporeal circuit. During treatment, blood from a patient is pumped through an arterial blood access connector 133 and the arterial line 124 to an inlet 129 of a dialyzer 128. Blood pump 127 provides the driving force for moving blood through the extracorporeal circuit. A venous air and blood sensor 148 can be included to detect air and blood in the venous line 126 prior to reaching the patient. A saline administration line can be connected to saline administration line connector 139 to provide saline directly into the extracorporeal circuit. Transducer protectors 145 and 147 can filter out any particulate matter in the venous line 126 and transducer protectors 141 and 143 can filter out any particulate matter in the arterial line 124. Pressure line connector 142 can connect the portions of the arterial line 124 inside and outside of the dialysis console, while pressure line connector 146 can connect the portions of the venous line 126 inside and outside of the dialysis console. Dialysate in a dialysate flow path is pumped through a dialysate inlet 132 to a dialysate outlet 131 of the dialyzer 128. Blood exits the dialyzer 128 through blood outlet 130 and is pumped back to the patient through venous line 126 and venous blood access connector 134. The arterial drip chamber 123 and venous drip chamber 125 can capture air present in the blood. The ability to capture air present in the blood depends in part upon a fluid level in each of the arterial drip chamber 123 and venous drip chamber 125.

The pneumatic manifold 101 can contain components for controlling the fluid level in both the arterial drip chamber 123 and venous drip chamber 125. The pneumatic manifold 101 contains several valves for controlling the fluid levels in the arterial drip chamber 123 and venous drip chamber 125, including a negative valve 106, a positive valve 105, a venous valve 104, and an arterial valve 103. The valves can be electrically powered such that an open or closed state can either be an activated or deactivated state. For example, activating a valve can result in a closed state whereupon deactivating the valve returns into an open state. Conversely, deactivating a valve can result in closed state whereupon activating, the valve is an open state. In certain embodiments, the valves can be activated by applying an electrical current to a solenoid valve. However, any type of valve can be used, and the valve can be activated by any means known in the art.

An internal conduit 102 connects the valves. Optionally, the pneumatic manifold 101 can contain a line clamp valve 107 for controlling a venous line clamp 137, which can stop blood flow through the venous line 126. Stopping blood flow through the venous line 126 may be performed in response to air detected in the venous line 126, or for any other reason necessitating stopping the blood flow. Lowering the fluid level in the arterial drip chamber 123 and venous drip chamber 125 can require an increase in pressure, which may introduce air into the extracorporeal circuit. If air is detected in the extracorporeal circuit, a controller (not shown) can automatically close the venous line clamp 137, stopping blood flow through the extracorporeal circuit. A pneumatic pump 108 provides the force necessary for raising and lowering the fluid levels in the arterial drip chamber 123 and venous drip chamber 125. The fluid levels in the arterial drip chamber 123 and venous drip chamber 125 depends on a pressure within each drip chamber. By selectively activating and deactivating the valves in the pneumatic manifold 101 while operating pneumatic pump 108, the pressure in the arterial drip chamber 123 and venous drip chamber 125 can be selectively controlled and/or modulated by raising or lowering the fluid level.

The pneumatic pump 108 can be positioned either inside or outside of the pneumatic manifold 101. If positioned outside of the pneumatic manifold 101, the pneumatic pump 108 can be positioned in a fluid line fluidly connected to an outlet 109 and an inlet 110 of the pneumatic manifold 101. The arterial valve 103 is fluidly connected to the internal conduit 102 and a fluid line 120, which fluidly connects to the arterial drip chamber 123. When activated, the arterial valve 103 creates a fluid pathway between the arterial drip chamber 123 and the internal conduit 102. Similarly, the venous valve 104 is fluidly connected to the internal conduit 102 and a fluid line 121, which fluidly connects to the venous drip chamber 125. When activated, the venous valve 104 creates a fluid pathway between the venous drip chamber 125 and the internal conduit 102. Depending on which of the positive valve 105 and negative valve 106 are activated, the pneumatic pump 108 will either pump air into the internal conduit 102, raising the pressure, or pump air out of the internal conduit 102, lowering the pressure. A pressure sensor 112 in the internal conduit 102 can determine the pressure. When activated, the arterial valve 103 or venous valve 104 form a pathway from the internal conduit 102 to the respective drip chambers, causing the fluid level to raise or lower depending on the pressure in the internal conduit 102. An arterial pressure sensor 111 and venous pressure sensor 114 can determine the pressure in the fluid lines 120 and 121, respectively. A flow restrictor 113 downstream of the arterial valve 103 and a flow restrictor 115 downstream of the venous valve 104 can prevent the pressure from changing too quickly. A vent 116 fluidly connected to the positive valve 105 can allow air to escape the pneumatic manifold 101 when the positive valve 105 is deactivated. A line clamp filter 117 filters air pulled into the pneumatic manifold 101 when the negative valve 106 is deactivated. A line clamp valve 107, fluidly connected to a venous line clamp 137 through fluid line 122 can also be included in the pneumatic manifold 101. Low pressure in the fluid line 122 will cause the venous line clamp 137 to close, blocking fluid flow through the venous line 126 when the line clamp valve 107 is activated. When deactivated, line clamp valve 107 forms a fluid pathway with vent 118, allowing a decrease in pressure in the fluid line 122, closing the venous line clamp 137. A line clamp check valve 119, which can be positioned either inside or outside of the pneumatic manifold 101, allows fluid to move only in a direction through the line clamp valve 107 from the positive valve 105 to the line clamp valve 107, while prevent fluid movement in the opposite direction.

Figure 2A:
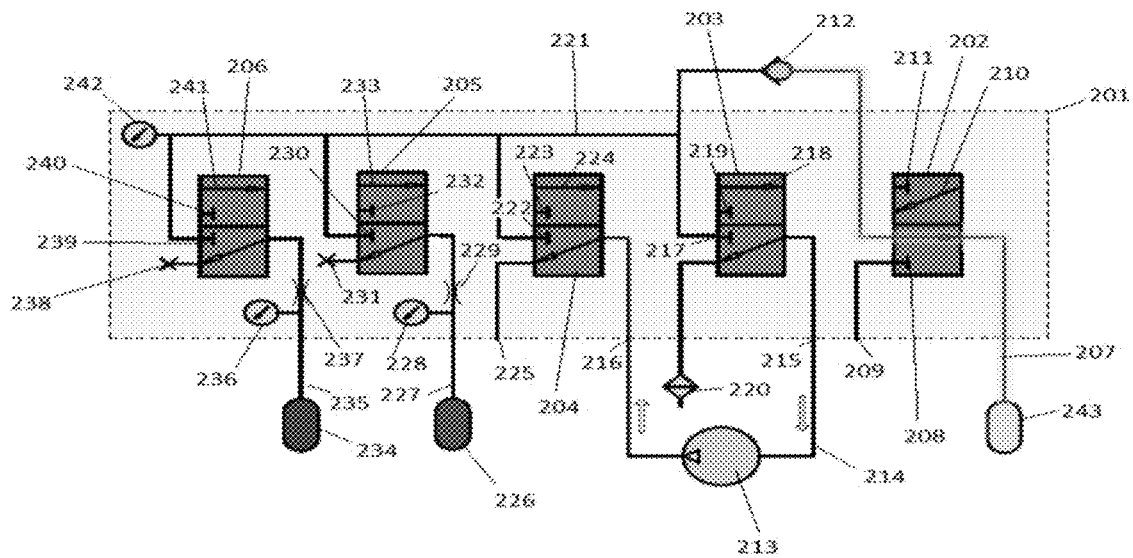
FIG. 2A is a schematic of a pneumatic manifold configured to hold open a venous line clamp.
Figure 2B:
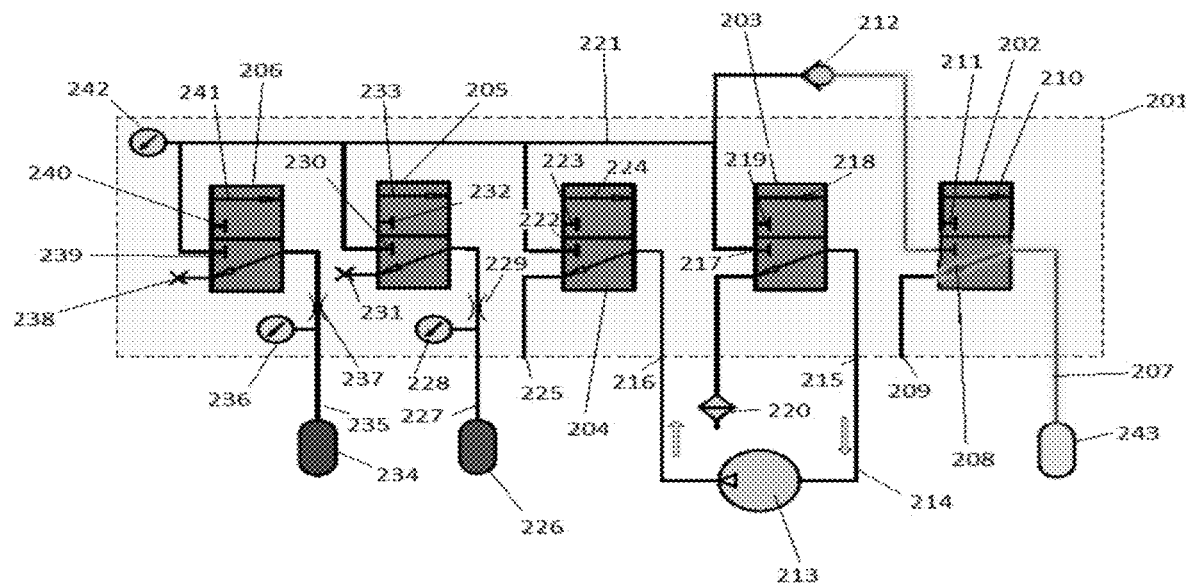
FIG. 2B is a schematic of a pneumatic manifold configured to close a venous line clamp.
Figure 2C:
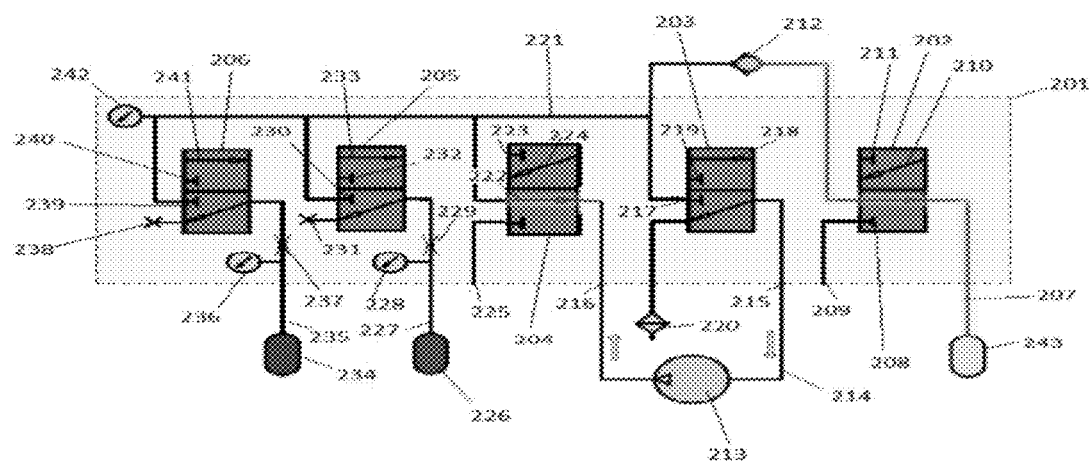
FIG. 2C is a schematic of a pneumatic manifold configured to open a venous line clamp.
Figure 2D:
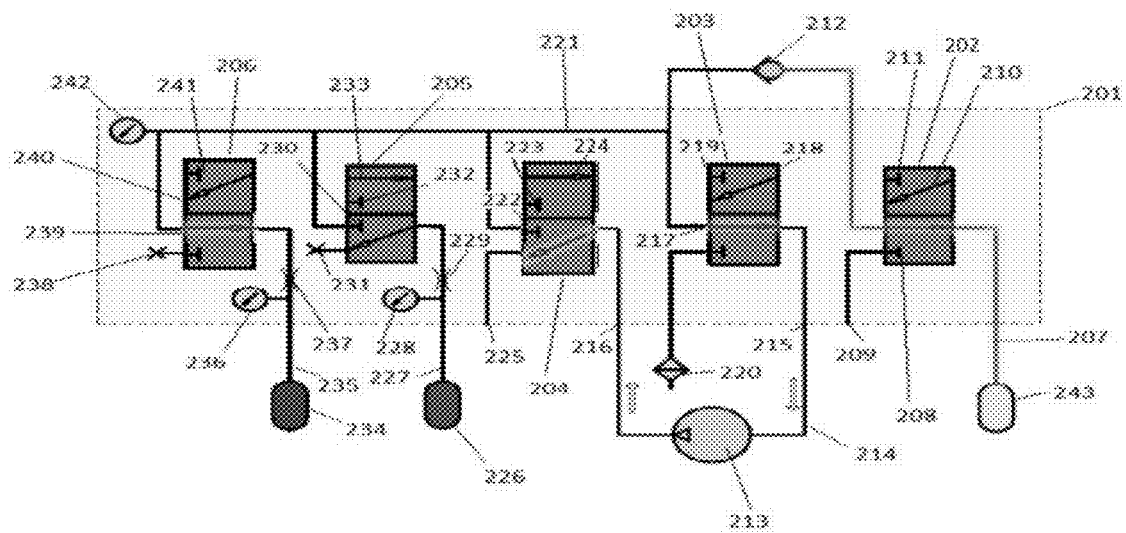
FIG. 2D is a schematic of a pneumatic manifold configured to raise a fluid level in an arterial drip chamber.
Figure 2E:
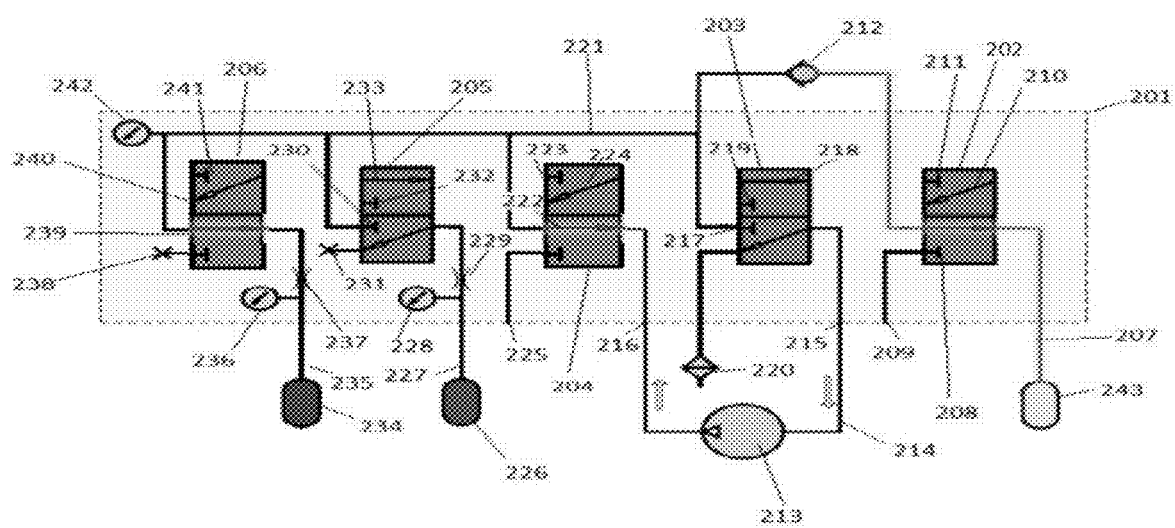
FIG. 2E is a schematic of a pneumatic manifold configured to lower a fluid level in an arterial drip chamber.

FIGS. 2A-E illustrate close-up views of the pneumatic manifold 201. FIG. 2A illustrates the valves selectively activated or deactivated for holding a venous line clamp 243 open; FIG. 2B illustrates the valves selectively activated or deactivated for closing the venous line clamp 243; FIG. 2C illustrates the valves selectively activated or deactivated for opening the venous line clamp 243; FIG. 2D illustrates the valves selectively activated or deactivated for raising a fluid level in an arterial drip chamber 234; and FIG. 2E illustrates the valves selectively activated or deactivated for lowering the fluid level in the arterial drip chamber 234.

In FIG. 2A, the line clamp valve 202 is shown as activated, forming a fluid pathway from the internal conduit 221 to a fluid line 207 fluidly connected to a venous line clamp 243. A line clamp check valve 212 prevents air from moving from the venous line clamp 243 into the rest of the internal conduit 221. The line clamp check valve 212 maintains the positive pressure in fluid line 207, keeping the venous line clamp 243 open. The positive valve 204 and negative valve 203 are shown as deactivated, preventing air from moving into or out of the internal conduit 221. The arterial valve 206 is deactivated, meaning that fluid line 235, fluidly connected to arterial drip chamber 234 is fluidly connected to a blockage 238 rather than connector 239 for connection to the internal conduit 221. The blockage 238 prevents changes in pressure in the arterial drip chamber 234, maintaining the fluid level. The venous valve 205 is also deactivated, meaning that venous line 227, fluidly connected to venous drip chamber 226 is fluidly connected to a blockage 231 rather than connector 230 for connection to the internal conduit 221. The blockage 231 prevents changes in pressure in the venous drip chamber 226, maintaining the fluid level. The selective activating and deactivating of the valves illustrated in FIG. 2A holds the venous line clamp 243 open, allowing fluid movement through the venous line (not shown) of an extracorporeal circuit.

In FIG. 2B, the line clamp valve 202 is deactivated, closing the venous line clamp 243. The fluid line 207 is connected to connector 208 when the line clamp valve 202 is deactivated. Connector 208 connects to fluid line 209, which includes a vent. The vent in fluid line 209 allows air to leave the fluid line 207, decreasing the pressure and closing venous line clamp 243.

In FIG. 2C, the line clamp valve 202 and positive valve 204 are activated. Activating positive valve 204 forms a fluid pathway, allowing pump 213 to pump air in through line clamp filter 220, through the deactivated negative valve 203, outlet 215, fluid line 214, inlet 216, and through connector 222 of the positive valve 204 into the internal conduit 221. The air flows through line clamp check valve 212 and activated line clamp valve 202 into fluid line 207, raising the pressure in fluid line 207 and opening venous line clamp 243. In FIG. 2C, both the arterial valve 206 and venous valve 205 are shown as deactivated. However, in certain embodiments, either the arterial valve 206 and venous valve 205 can be activated while opening the venous line clamp 243, allowing the fluid level in the arterial drip chamber 234 or venous drip chamber 226 to be lowered simultaneously.

In FIG. 2D, both the negative valve 203 and the arterial valve 206 are activated, raising the fluid level in the arterial drip chamber 234. Activating the negative valve 203 forms a fluid pathway from the internal conduit 221 through connector 217 to fluid line 214. Activating the arterial valve 206 forms a fluid pathway from arterial drip chamber 234 through fluid line 235 and connector 239 to internal conduit 221. The fluid pathway allows pump 213 to pump air from the arterial drip chamber 234, through the internal conduit 221 and deactivated positive valve 204 to vent 225, lowering the pressure in arterial drip chamber 234 and raising the fluid level. Arterial pressure sensor 236 can determine the pressure in the fluid line 235, and pressure sensor 242 can determine the pressure in internal conduit 221. A pressure difference between arterial pressure sensor 236 and pressure sensor 242 confirms that the pump 213 is properly operating when raising the fluid level in the arterial drip chamber 234. Raising the fluid level in the arterial drip chamber 234 should result in a pressure at pressure sensor 242 that is lower than the pressure at arterial pressure sensor 236. If the pressure difference is not detected, an alert can be generated. A spike in pressure measured by pressure sensor 242 as compared to arterial pressure sensor 236 or a venous pressure sensor 228 could indicate an obstruction in the arterial valve 206 or venous valve 205. Further, because the blood pump (not shown) is generally a pulsatile pump, the pressure as monitored at arterial pressure sensor 236 and venous pressure sensor 228 should give a pulsatile response when the blood pump is operating. A static pressure may also indicate an occlusion. If an occlusion is detected, an alert can be generated by the system. A flow restrictor 237 prevents the fluid level in the arterial drip chamber 234 from rising too rapidly. In FIG. 2D, the line clamp valve 202 is activated, opening the venous line clamp 243. If the extracorporeal circuit has the arterial drip chamber 234 positioned upstream of the blood pump, the venous line clamp 243 can be either opened or closed when raising the fluid level of the arterial drip chamber 234. However, the venous line clamp 243 must be open when raising the fluid level in the arterial drip chamber 234 if the arterial drip chamber 234 is located downstream of the blood pump. For an arterial drip chamber 234 upstream of the blood pump, the pressure is normally a negative value in the arterial drip chamber 234 when the blood pump is operating during patient connected treatment. Therefore when raising the fluid level of the arterial drip chamber 234, the pressure at pressure sensor 242 becomes more negative. However, for an arterial drip chamber 234 downstream of the blood pump, the drip chamber pressure is normally positive when the blood pump is operating during patient connected treatment. Therefore, when raising the fluid level in the arterial drip chamber 234, the amount of force required to raise the fluid level can be higher due to the positive pressure in the arterial drip chamber 234 and the pressure difference between pressure sensor 242.

In FIG. 2E, both the positive valve 204 and the arterial valve 206 are activated, lowering the fluid level in the arterial drip chamber 234. Activating the positive valve 204 forms a fluid pathway from the internal conduit 221 through connector 222 to fluid line 214. Activating the arterial valve 206 forms a fluid pathway from arterial drip chamber 234 through fluid line 235 and connector 239 to internal conduit 221. The fluid pathway allows pump 213 to pump air from the line clamp filter 220, through deactivated negative valve 203 to fluid line 214 and then through inlet 216 in connector 222 in positive valve 204. The air can then flow through internal conduit 221, to arterial drip chamber 234 through fluid line 235, raising the pressure in arterial drip chamber 234 and lowering the fluid level. Lowering the fluid level in the arterial drip chamber 234 should result in a pressure at pressure sensor 242 that is higher than the pressure at arterial pressure sensor 236. If the pressure difference is not detected, an alert can be generated. In FIG. 2E, the line clamp valve 202 is activated, opening the venous line clamp 243. If the extracorporeal circuit has the arterial drip chamber 234 upstream of the blood pump the venous line clamp 243 can be either opened or closed when lowering the fluid level of the arterial drip chamber 234. However, the venous line clamp 243 must be open when lowering the fluid level in the arterial drip chamber 234 if the arterial drip chamber 234 is located downstream of the blood pump.

In order to adjust the level of either drip chamber, a fluid reservoir is needed to either supply the fluid when raising the drip chamber fluid level or to accept the fluid when lowering a drip chamber fluid level. If the blood pump is not operating when a post-blood pump arterial drip chamber 234 or venous drip chamber 226 fluid level is adjusted, the patient can serve as the fluid reservoir. As such, the venous line clamp should be open to allow the patient to serve as a fluid source for raising the fluid level or to allow the patient to accept fluid when lowering the drip chamber fluid level. In certain embodiments, the ability to adjust the fluid level may be disabled when no fluid reservoir is available because operating the level adjust with no fluid reservoir may result in drip chamber pressure changes without any fluid level changes, triggering a pressure alarm.

FIGS. 2D and 2E illustrate the control of the valves in the pneumatic manifold 201 for raising or lowering the fluid level in the arterial drip chamber 234. One of skill in the art will understand the same controls can be used to raise or lower the fluid level in the venous drip chamber 226 with the venous valve 205 activated instead of the arterial valve 206. Flow restrictor 229 prevents the fluid level in the venous drip chamber 226 from being changed too quickly, while venous pressure sensor 228 can ensure the pump 213 is functioning properly when venous valve 205 is activated. The fluid levels in both the venous drip chamber 226 and arterial drip chamber 234 can be both raised or lowered simultaneously by activating both the venous valve 205 and the arterial valve 206. However, the fluid level in the venous drip chamber 226 cannot be raised while simultaneously lowering the fluid level in the arterial drip chamber 234 or vice versa.

Raising or lowering the fluid level in the venous drip chamber 226 and arterial drip chamber 234 can result in changes in pressure in the extracorporeal circuit. The changes in pressure could cause a transmembrane pressure across the dialyzer to increase beyond a safe limit. Pressure sensors can measure the transmembrane pressure and prevent changes to drip chamber fluid levels if the transmembrane pressure is within a set range of the maximum allowable transmembrane pressure for the dialyzer.

The valves of the pneumatic manifold 201 can be operated by a programmable controller (not shown). The controller can automatically adjust the fluid levels in the venous drip chamber 226 and arterial drip chamber 234 as necessary by activating and deactivating the valves as described to maintain a desired fluid level during treatment. The controller can be programmed to maintain a set fluid level in the venous drip chamber 226 and arterial drip chamber 234 and to prevent unwanted fluid level changes.

Connectors 210-211 of line clamp valve 202, connectors 218-219 of negative valve 203, connectors 223-224 of positive valve 204, connectors 232-233 of venous valve 205, and connectors 240-241 of arterial valve 206 are unused portions of the valves, and in certain embodiments can be eliminated.

Figure 3:
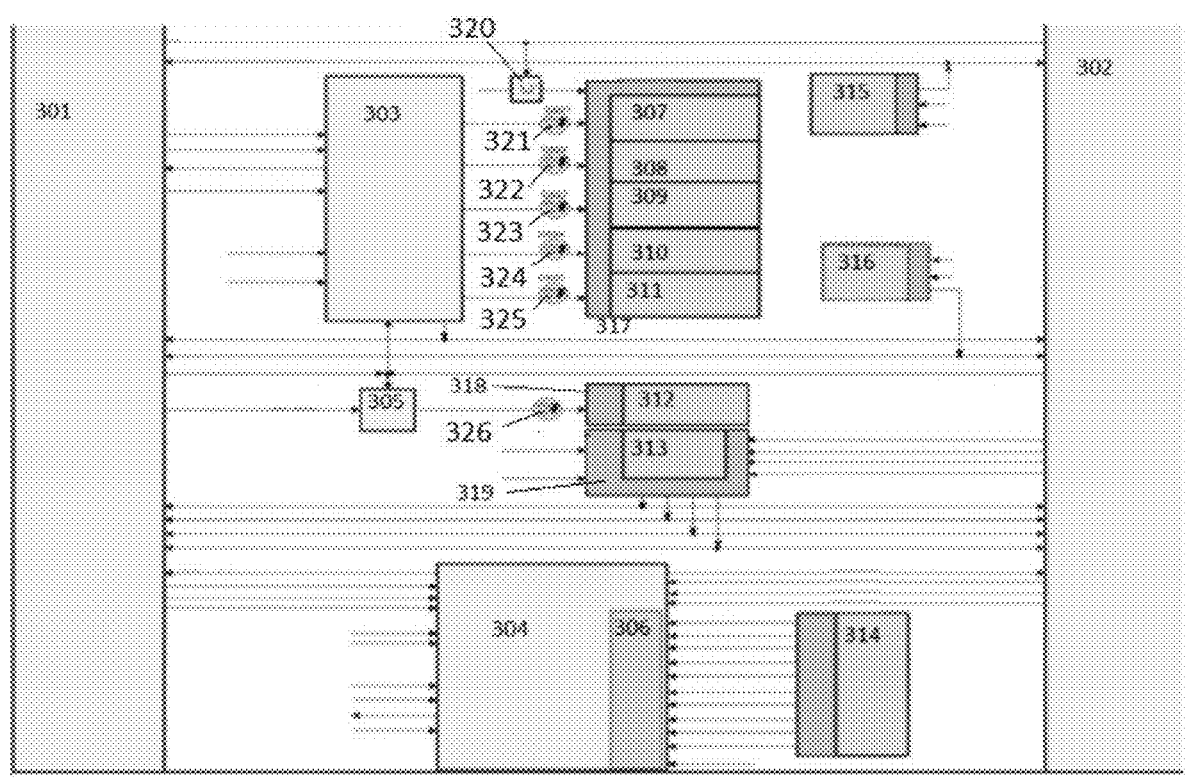
FIG. 3 is a schematic showing communication between components of the pneumatic manifold.

FIG. 3 illustrates a non-limiting example of communication between the controller or controllers and the described components. The communication is shown generally by line arrows connecting the respective components. The controller can include a control processor 301, as well as a protective processor 302. A driver 303 can be in communication with the control processor 301 and controls the valves of the pneumatic manifold, including the line clamp valve 307, the venous valve 308, the arterial valve 309, the positive valve 310 and the negative valve 311, represented by valve set 317. The driver 303 can be any driver chip known in the art, including a TI DRV8860 driver chip. Both the control processor 301 and protective processor 302 can enable the driver 303 to operate any of the valves in valve set 317. Either the control processor 301 or protective processor 302 can disable all valves in valve set 317, however, only the control processor 301 can turn on or off individual valves. Field effect transistor 320 can be used to supply power to each of the valves in valve set 317. Optional light emitting diodes 321-325 can be included to indicate application of electrical power to each of the valves 307-311, respectively.

The pump 312 can enabled or disabled by either of the control processor 301 and protective processor 302, allowing the pump to be started or shut down as needed during therapy or if required for safety. However, both the control processor 301 and protective processor 302 must send an enable signal to the pump 312 for the pump 312 to run. A field effect transistor 305 can be included to supply power to the pump 312. Connector board 318 can be included for communication between the pump 312, control processor 301, and protective processor 302. A light emitting diode 326 can be included to indicate the application of power to the pump 312.

Pressure sensors, illustrated as pressure sensor set 314 can include an arterial pressure sensor, a venous pressure sensor, and an internal conduit pressure sensor. The pressure sensors are in communication with the control processor 301 and protective processor 302 through differential amplifier 304. A multiplexer 306 can be included for communication with the pressure sensors of pressure sensor set 314.

Level sensors 313 can monitor the fluid level in the arterial drip chamber and venous drip chamber. The level sensors 313 are in communication with both the control processor 301 and protective processor 302 to control the fluid level in each drip chamber. Connector board 319 can be included for communication between the level sensors 313, control processor 301, and protective processor 302. The venous line clamp, and an arterial line clamp can be monitored by a venous line clamp sensor 315 and an arterial line clamp sensor 316. The line clamp sensors can monitor the state of the line clamps to ensure the line clamps are functioning properly.

The arrows shown in FIG. 3 that do not connect to either the control processor 301 or the protective processor 302 represent either wires from a power supply to the components, or ground wires from the components. The voltages applied between the components and the power supply or ground can vary depending on the needs and requirements of the particular electronics used. In one non-limiting example, the six arrows to and from differential amplifier 304 that do not connect to either the control processor 301 or the protective processor 302 can represent +3.3 volts, a digital ground, +1.5 volts, +5 volts, an analog ground, and −5 volts, respectively.

Figure 4:
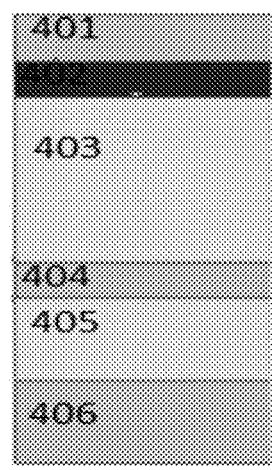
FIG. 4 is an illustration of possible states for a venous line clamp.

FIG. 4 illustrates potential line clamp positions that can be monitored by the line clamp sensors. Position 401 is an open position. Position 401 is a calibrated range of positions. If in the open range, the venous line clamp may not be in physical contact with the blood tubing. Position 402 is a recharge position. The recharge position is a calculated offset from the last position in the open range. In the recharge position 402, the venous line clamp may not occlude any venous line that might be in the venous line clamp. If the recharge state is reached while the controller commanded venous line clamp state is open, the pressure holding the clamp open will be increased in order to return the clamp to the open position. Position 403 is a transient position between the lower limit of the recharge range and the top of the closed on line range. Position 403 is expected to be a transient condition, and should only be detected when the venous line clamp is in the process of opening or closing. If blood tubing is present in the venous line clamp while in transient position 403, the blood tubing can be partially occluded which could result in hemolysis of the blood. Therefore the venous line clamp should never remain in position 403 while blood is in the venous patient line. Position 404 is a closed on line position. The closed on line position 404 is a calibrated range of positions. The venous line is within an acceptable range of the calibrated position for the clamp to fully occlude the blood tubing to a level sufficient to prevent liquid flow. Position 405 is a transient position between closed on line and closed. Position 405 is expected to be a transient condition, and should only be detected when the clamp is in the process of opening or closing. Position 406 is a closed position. In the closed position 406, the venous line clamp is in a calibrated fully closed position without the presence of tubing.

During pre-treatment, the system can verify the functionality and operational status of the venous line clamp. When the operator initiates the start of treatment preparation, before installation of the tubing set, the system commands the venous line clamp to the open state in position 401, and verifies that the venous line clamp sensor detects the venous line clamp to be in the open range. The system then commands the venous line clamp to the closed state in position 406, and verifies that the venous line clamp sensor detects the venous line clamp to be in the closed range. The venous line clamp sensor can be monitored to ensure the venous line clamp closes within a pre-determined time window. If any part of venous line clamp test fails, the system can generate an alarm. The operator may be allowed to reset the alarm, and retry the test.

After a first subset of tests are successfully completed, the venous line clamp is opened and the operator is prompted to install the blood disposables, which includes the blood tubing set. Once the user confirms that the disposables are installed, the system commands the venous line clamp to the closed state, and verifies that the venous line clamp sensor detects the venous line clamp to be in the closed on line range in position 404. The venous line clamp sensor will be monitored to ensure the venous line clamp closes on the tube within a pre-determined time window. Finally the system tests that the clamp can be commanded to the open state in position 401, and verifies that the venous line clamp sensor detects the clamp to be in the open range. If any part of the venous line clamp test fails, the system can generate an alarm. The operator may be allowed to reset the alarm, and retry the test.

Figure 5:
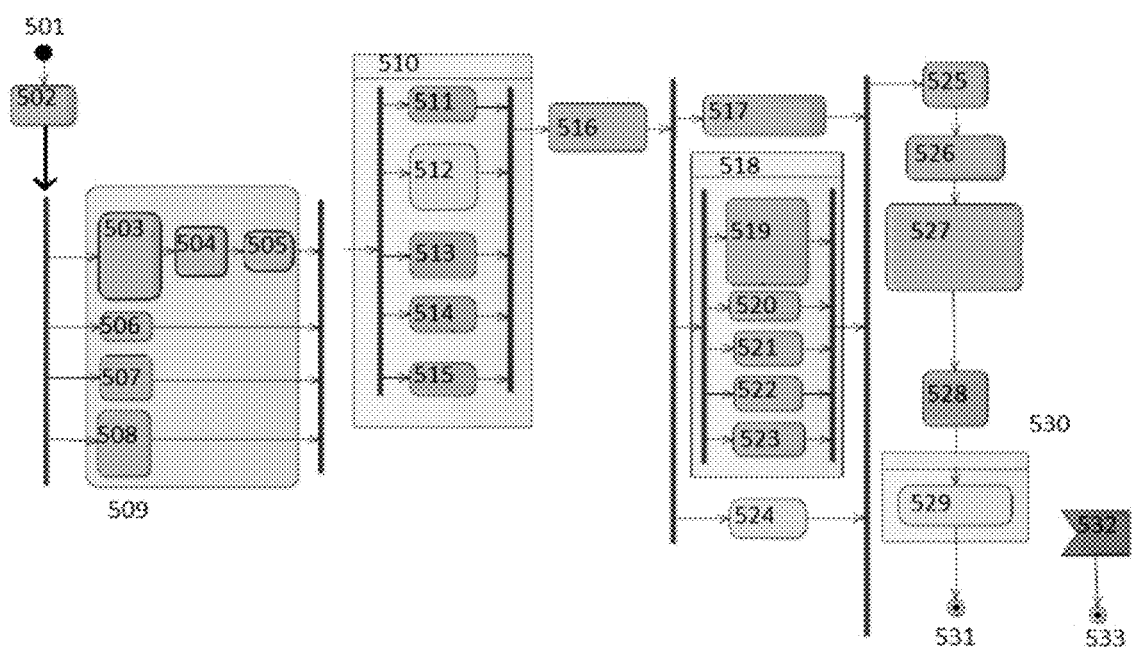
FIG. 5 is a workflow using the pneumatic manifold for setting up a therapy session.

The monitoring of the venous line clamp can be initiated in parallel with the activation of the remaining blood set monitors (i.e., blood pump, blood line pressures, and heparin pump) as illustrated in FIG. 5. The system continues to monitor the venous line clamp until the user confirms that the patient has been disconnected (following a completed blood return process). Once activated, the monitoring of the venous line clamp activity monitors the position of the venous line clamp and resolves the position to one of the six ranges illustrated in FIG. 4. Monitoring the venous line clamp can occur on both the control processor 301 and protective processor 302 illustrated in FIG. 3. A monitor venous line clamp protective protocol can be used by the control processor to send notifications of a change in the state to the protective processor. The monitoring criteria can include (1) determining that the venous line clamp closes on tubing within the time required to prevent an air hazard from reaching the patient, such as 2 seconds; (2) determining that the blood tubing is properly installed in the VLC during the course of the treatment; (3) ensuring there are no hardware or software faults with the line clamp system during treatment; (4) ensuring that the VLC attains the expected range when commanded; and (5) ensuring the venous line clamp remains in the state and position the venous line clamp was last commanded to. The monitoring is performed by both the control and protective system, and either can generate an alarm relating to the venous line clamp condition.

Too frequent inflations of the venous line clamp from the recharge position 402 to the open position 401 can be indicative of an air leak in the venous line clamp apparatus. If an air leak is detected before the system is in a hemodialysis patient connection state, a blood side malfunction alarm can be raised and the system can disallow further processing. If the leak is detected after the system enters hemodialysis patient connection state, the treatment can be allowed to continue. The operator may choose to reset an instance of the alarm, or may chose for the machine to pause the audio component of the alarm until the end of the treatment.

During the venous line clamp tests, both the control processor and protective processor check the position of the venous line clamp, as reported by the venous line clamp sensor. If the venous line clamp sensor does not detect the correct position, or the position is not reached within the expected time, either the control or protective processors can generate an alarm. The control processor can responsible for reporting the venous line clamp test results to a user interface, which can be responsible for logging the T1 test results. The control processor can be responsible for monitoring for alarm conditions and reporting the alarm conditions to the user interface. The user interface is responsible for reporting the alarm conditions to the user and allowing the user to reset alarms if appropriate.

FIG. 5 illustrates a non-limiting embodiment of a work flow can be conducted prior to initiating treatment. The initial state is 501. Treatment preparation begins in step 502. A series of tests on a blood side of a dialysis system can begin in step 509. Test 503 is a zero comparison test of the venous pressure sensor and the arterial pressure sensor, as well as the pressure sensor in the internal conduit. While exposed to atmospheric pressure, the pressure sensors should provide a "zero" reading relative to a pressure sensor measuring atmospheric pressure. Test 504 is a venous line clamp open/closed test, ensuring that the venous line clamp fully opens and fully closes. Passing the venous line clamp open/closed test shows that the pump, positive valve, and line clamp valve are properly functioning. Test 505 is an arterial and venous level test. The arterial and venous level test 505 can begin by activating the negative valve and arterial valve and activating the pump. A pressure change of a predetermined amount in the internal conduit should occur. If the necessary pressure change occurs, the pump is stopped while the arterial valve is kept activated. The pressure in the internal conduit should drop into a predetermined range within a predetermined time period. The negative valve can then be deactivated, the positive valve activated, and the pump started. A pressure change in the internal conduit can occur. The arterial and venous level test 505 can continue with the venous test. The negative valve and venous valve can be activated and the pump activated. A pressure change of a predetermined amount in the internal conduit should occur. If the necessary pressure change occurs, the pump is stopped while the venous valve is kept activated. The pressure in the internal conduit should drop into a predetermined range within a predetermined time period. The negative valve can then be deactivated, the positive valve activated, and the pump started. A pressure change in the internal conduit should again occur. If any of the necessary pressure changes do not occur, an alarm can be generated by the system. The system can prompt the user to retry the test. If the system continues to fail the test, treatment can occur without the ability to use the pneumatic manifold to adjust the arterial or venous drip chamber fluid levels. During the test, only the pressure in the internal conduit should change due to the flow restrictors at the air outlets. If the arterial pressure sensor or venous pressure sensor change in sync with the internal conduit pressure, the system can inform the user to check for either a wetted internal transducer protector or a clamped blood tubing pressure line connected to the pressure port. The venous line clamp test described with reference to FIG. 4 can also be conducted during the arterial and venous level test 505.

In test 506, the blood pump is shut down to ensure proper control of the blood pump. If a heparin pump is being used, the heparin pump is fully opened in test 507. In test 508, optical sensors in the arterial and venous lines are read to ensure no tubing is installed.

The series of steps illustrated as 510 can be carried out to activate the blood side of the dialysis system for installation of consumables. In step 511, the venous line clamp is opened. In step 512 the pre-treatment blood set monitors are activated. In step 513, the blood pump is enabled in a reverse direction. In step 514, the drip chamber level adjust is activated. In step 515, the heparin pump is activated, if a heparin pump is being used. After the steps in 510, the user can be notified that the system is ready to install blood disposable components in step 516. In step 517 the system can verify the pump door as a background task.

The series of steps illustrated as 518 can be carried out to install disposables and perform pre-prime tasks. In step 519, the operator can configure the extracorporeal circuit, install the blood tubing, and as applicable, install the dialyzer, saline, saline administration set, waste bag, and heparin. The venous line is primed in step 520, and the venous line connected to the dialyzer in step 521. The venous drip chamber level is adjusted in step 522. The arterial line is connected to the dialyzer in step 523. If heparin is being used, the user can initialize the heparin pump in step 524. After the blood installation process is completed, the user can be asked to confirm. The user confirms the blood consumables are installed in step 525 and obtains the extracorporeal circuit configuration in step 526. In step 526, the user is prompted to confirm or enter the dialyzer and blood set configurations. The user can be asked whether the dialyzer is being used for the first time, or whether the dialyzer is being reused with peracetic acid or formalin. The user can be asked whether the blood set is 6 or 8 mm, or any other size. The user can be asked whether the arterial drip chamber is upstream or downstream of the blood pump. The user can also be asked whether the priming method is saline or transmembrane. Steps 525 and 526 can be done in parallel or sequentially.

Test 527 includes any open tasks, including verification that the pump door is closed, that the venous line clamp is closed on tube, reading the optical sensors to confirm tubing is installed, and activation of monitoring the optical sensors. Each step in test 527 can have a retry or stop treatment option. In step 528, the disposable preparation can continue.

After preparing the disposables in step 528, the extracorporeal circuit can be flushed and primed in step 529, shown as series 530. After flushing the extracorporeal circuit, an additional test to verify the response of the arterial pressure sensor and venous pressure sensor can be conducted as part of series 530. The blood pump can be activated in reverse, which will generate changes in the static blood line pressures as measured by the arterial and venous pressure sensors.

Figure 6:
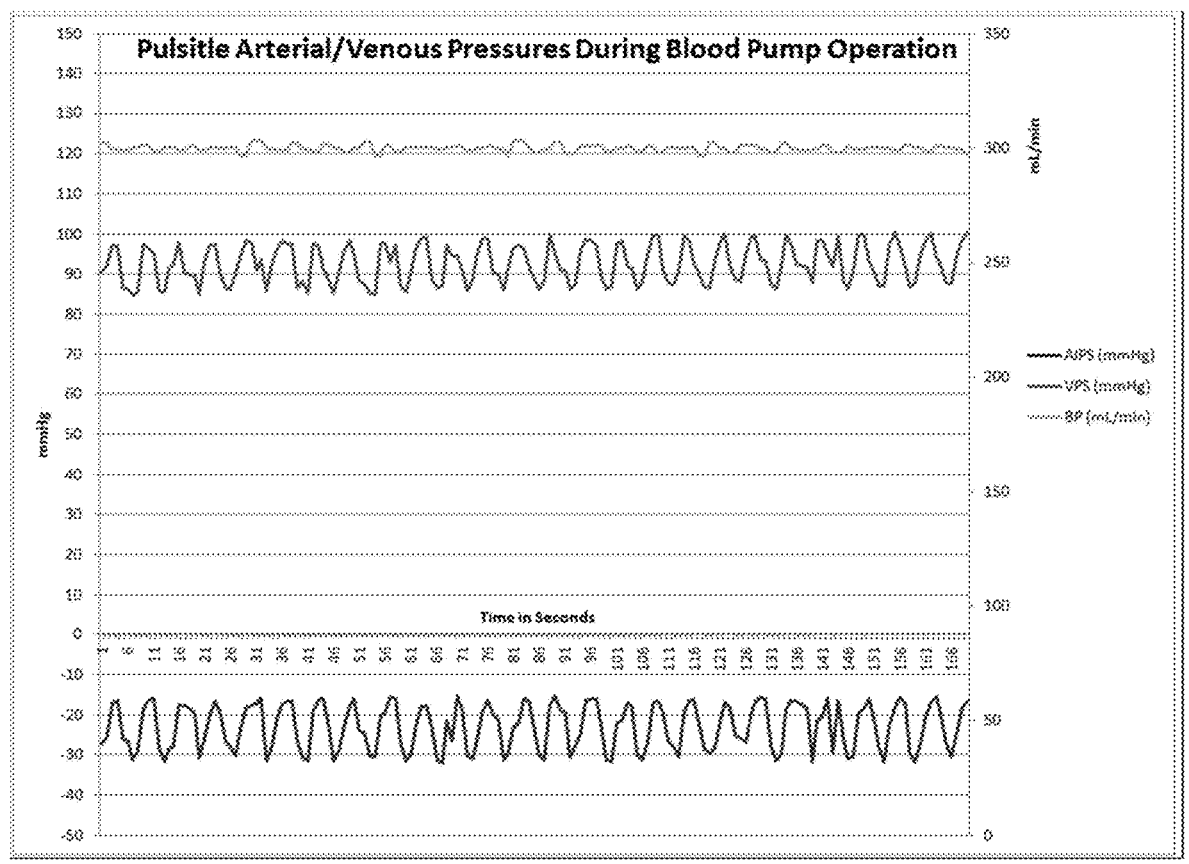
FIG. 6 is a graph showing pressures in the pneumatic manifold as a function of blood pump rate.

An example of the response with drip chambers upstream of the blood pump is shown in FIG. 6. Because the blood pump is a pulsatile pump, the pressure should show a pulsatile response. If a pulsatile pressure profile change is not detected during the test, an alert indicating that the arterial and venous level connection should be checked can be generated. In FIG. 6, the bottom line is the blood pump rate, the middle line is the pressure measured by an venous pressure sensor in the pneumatic manifold, and the top line is the pressure measured by a venous pressure sensor in the pneumatic manifold. The x-axis in FIG. 6 is time in seconds, and the y-axis is both pressure relative to atmospheric pressure and blood pump rate relative to the initial blood flow rate. Because the blood pump is running in a reverse direction, the value for the blood pump rate is negative in FIG. 6. When the blood pump is activated in reverse, the venous pressure decreases. As illustrated in FIG. 6, both the arterial pressure and venous pressure show a pulsatile profile after reversal of the blood pump. One of skill in the art will understand that when using an arterial drip chamber downstream of the blood, pump, the pressure change will be in a positive direction and will mirror the venous response. If all tests are passed, the system can be placed in a final state 531 until treatment starts. If any tests are not passed, treatment preparation can be halted in step 532, and the system placed in a non-final state 533.

Figure 7:
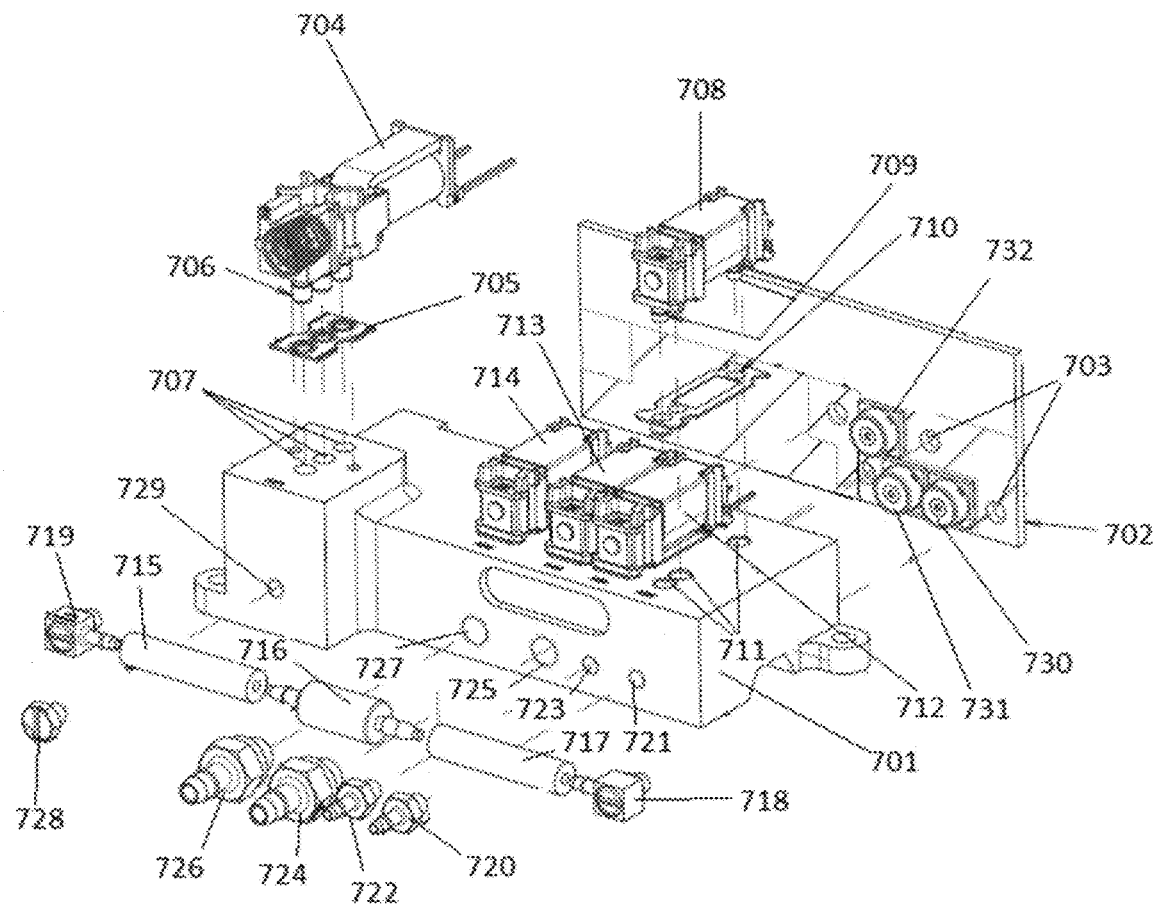
FIG. 7 is an exploded view of a non-limiting embodiment of a pneumatic manifold.

FIG. 7 illustrates an exploded view of a non-limiting embodiment of a pneumatic manifold. The pneumatic manifold can include a base 702 and a body 701. Holes 703 in the base 702 can be used to attach the base 702 to the body 701 by screws or other fasteners. The pneumatic manifold can include an arterial valve 708, a venous valve 712, a positive valve 713, a negative valve 714, and a line clamp valve 704. In FIG. 7, the venous valve 712, positive valve 713, and negative valve 714 are illustrated attached to the body 701, while the arterial valve 708 and line clamp valve 704 are shown unattached. The line clamp valve 704 can include connectors 706 which can connect to the body 701 through gasket 705 and openings 707. Similarly, the arterial valve 708 can include connectors 709 for connection to the body 701 through gasket 710 and openings 711. Outlet 730 can connect the arterial valve 708 to an arterial drip chamber, outlet 731 can connect the venous valve 712 to a venous drip chamber, and inlet 732 can connect a pump to the positive valve 713. Additional inlets and outlets (not shown) can be provided for connection to the negative valve 714 and line clamp valve 704.

As illustrated in FIG. 7, in certain embodiments the internal conduit can be segmented into a first segment 715, a second segment 716, and a third segment 717. Alternatively, the internal conduit can be provided as a single conduit through the pneumatic manifold. Fitting 720 can connect the internal conduit to arterial valve 708 through opening 721. Fitting 722 can connect the internal conduit to venous valve 712 through opening 723. Fitting 724 can connect the internal conduit to positive valve 713 through opening 725. Fitting 726 can connect the internal conduit to negative valve 714 through opening 727. Fitting 728, which in certain embodiments can serve as a check valve, can connect the internal conduit to line clamp valve 704 through opening 729.

Figure 8A:
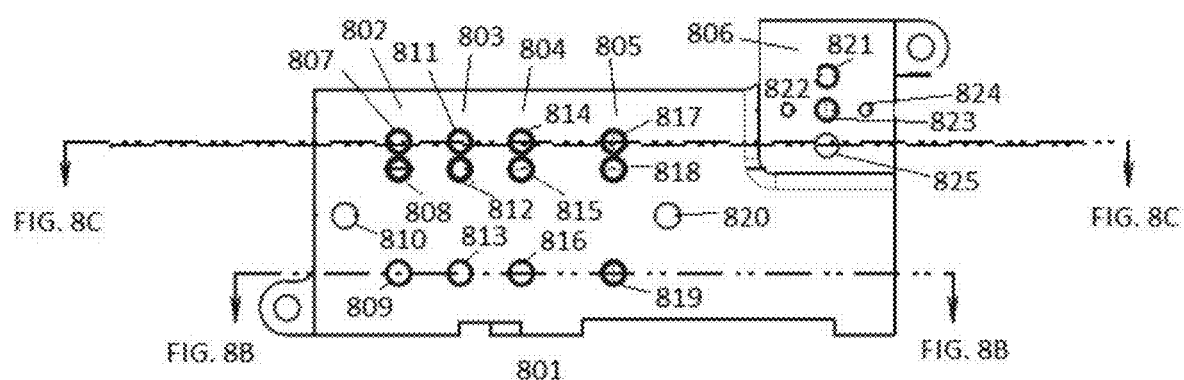
FIGS. 8A-C are design drawings of a pneumatic manifold.

FIG. 8A shows a non-limiting design of a pneumatic manifold 801. The pneumatic manifold 801 can include an arterial valve in position 802, a venous valve in position 803, a positive valve in position 804, a negative valve in position 805, and a line clamp valve in position 806. Openings 807 and 808 connect the arterial valve to an internal conduit, while opening 809 connects the arterial valve to an arterial drip chamber. Openings 811 and 812 connect the venous valve to the internal conduit, while opening 813 connects the venous valve to a venous drip chamber. Openings 814 and 815 connect the positive valve to the internal conduit, while opening 816 connects the positive valve to an inlet and a fluid line having a pump. Openings 817 and 818 connect the negative valve to the internal conduit, while opening 819 connects the negative valve to an outlet and a fluid line having a pump. The line clamp valve can be connected to the internal conduit through openings 821 and 823, and connected to a venous line clamp through opening 825.

Figure 8B:
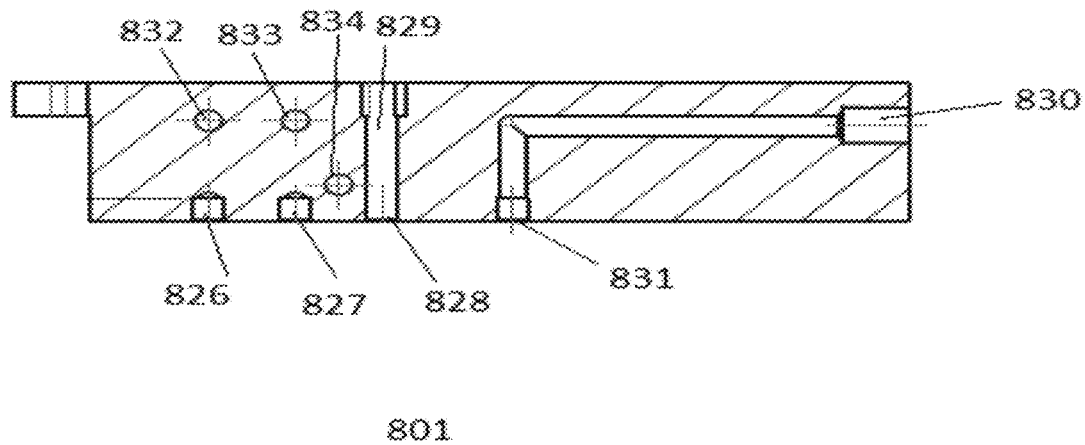

FIG. 8B is a cross section of the bottom of the pneumatic manifold 801 illustrated in FIG. 8A. Outlet 831 can connect to the negative valve through connector 830. Outlet 831 can be fluidly connected to a fluid line having a pump. The fluid line can also be fluidly connected to inlet 828, which is connected to the positive valve through connector 829. The venous valve can connect to a venous drip chamber through connector 827, and the arterial valve can connect to an arterial drip chamber through connector 826.

Figure 8C:
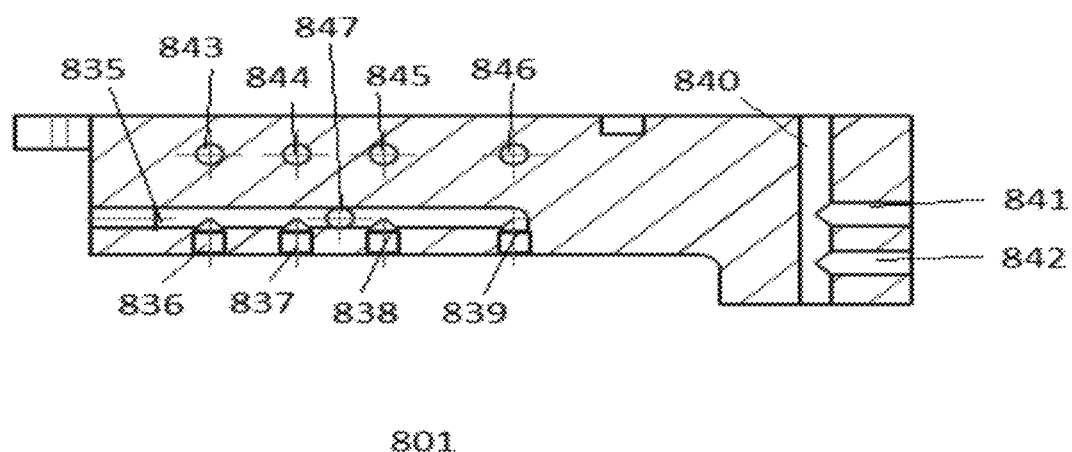

FIG. 8C is a cross section of the upper portion of the pneumatic manifold 801 illustrated in FIG. 8A. An internal conduit 835 can be fluidly connected to the arterial valve through connector 836, the venous valve through connector 837, the positive valve through connector 838, and the negative valve through connector 839. The line clamp valve can be fluidly connected to an internal conduit 840 through connectors 841 and 842.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

We claim:

1. A pneumatic manifold, comprising:
an internal conduit;
a first fluid line fluidly connected to the internal conduit; the first fluid line fluidly connectable to a venous drip chamber in an extracorporeal circuit of a dialysis system;
a second fluid line fluidly connected to the internal conduit; the second fluid line fluidly connectable to an arterial drip chamber in the extracorporeal circuit of the dialysis system;
a venous valve fluidly connecting the first fluid line to the internal conduit;
an arterial valve fluidly connecting the second fluid line to the internal conduit;
a negative valve fluidly connecting the internal conduit to an outlet;
a positive valve fluidly connecting the internal conduit to an inlet;
the inlet and outlet fluidly connectable by a third fluid line containing a pump; and
a controller selectively activating or deactivating the venous valve, arterial valve, positive valve, and negative valve; the controller controlling a fluid level in the venous drip chamber and arterial drip chamber by activating or deactivating the valves.

2. The pneumatic manifold of claim 1, further comprising a line clamp valve; the line clamp valve fluidly connecting the internal conduit and a second outlet; the second outlet fluidly connectable to a line clamp in the extracorporeal circuit.

3. The pneumatic manifold of claim 1, further comprising a vent fluidly connected to the positive valve.

4. The pneumatic manifold of claim 2, further comprising a vent fluidly connected to the line clamp valve.

5. The pneumatic manifold of claim 2, further comprising a line clamp check valve positioned between the positive valve and the line clamp valve; the line clamp check valve allowing fluid to move only in a direction from the positive valve to the line clamp valve.

6. The pneumatic manifold of claim 1, further comprising a first flow restrictor positioned between the venous valve and the first fluid line; and a second flow restrictor positioned between the arterial valve and the second fluid line.

7. The pneumatic manifold of claim 1, further comprising a venous pressure sensor positioned between the venous valve and the first fluid line; and an arterial pressure sensor positioned between the arterial valve and the second fluid line.

8. The pneumatic manifold of claim 1, further comprising a pressure sensor positioned in the internal conduit.

9. The pneumatic manifold of claim 1, further comprising a line clamp filter; the line clamp filter fluidly connected to the negative valve and a second inlet of the pneumatic manifold; wherein the internal conduit is fluidly connected to the outlet when the negative valve is activated and fluidly connected to the line clamp filter when the negative valve is deactivated.

10. The pneumatic manifold of claim 2, further comprising a vent fluidly connected to the line clamp valve; wherein the internal conduit is fluidly connected to the second outlet when the line clamp valve is activated and fluidly connected to the vent when the line clamp valve is deactivated.

11. A method of controlling a fluid level in an arterial drip chamber and/or venous drip chamber, comprising:
selectively activating or deactivating one or more valves in the pneumatic manifold of claim 1.

12. The method of claim 11, wherein the step of controlling the fluid level in the arterial drip chamber comprises the step of raising the fluid level in the arterial drip chamber by selectively activating the negative valve and the arterial valve.

13. The method of claim 11, wherein the step of controlling the fluid level in the arterial drip chamber comprises the step of lowering the fluid level in the arterial drip chamber by selectively activating the positive valve and the arterial valve.

14. The method of claim 11, wherein the step of controlling the fluid level in the venous drip chamber comprises the step of raising the fluid level in the venous drip chamber by selectively activating the negative valve and the venous valve.

15. The method of claim 11, wherein the step of controlling the fluid level in the venous drip chamber comprises the step of lowering the fluid level in the venous drip chamber by selectively activating the positive valve and the venous valve.

16. The method of claim 11, further comprising the step of stopping blood flow in a venous line of the extracorporeal circuit by selectively activating the positive valve and a line clamp valve in the pneumatic manifold; the line clamp valve fluidly connecting the internal conduit and a second outlet; the second outlet fluidly connected to a venous line clamp.

17. The method of claim 16, wherein the step of stopping blood flow in the venous line of the extracorporeal circuit is performed in response to air detected in the venous line.

18. The method of claim 16, wherein the step of controlling the fluid level in the venous drip chamber comprises first opening the venous line clamp and then activating the venous valve and either the positive valve or negative valve.

19. The method of claim 16, wherein the step of controlling the fluid level in the arterial drip chamber comprises first opening the venous line clamp and then activating the arterial valve and either the positive valve or negative valve.

20. The method of claim 11, the controller programmed to maintain a set fluid level in the arterial drip chamber and/or venous drip chamber by selectively activating the one or more valves.

21. The method of claim 11, further comprising the steps of monitoring a pressure in the pneumatic manifold in the first fluid line, the second fluid line, or both; and generating an alarm indicating an occlusion if the pressure in the first fluid line, the second fluid line, or both does not show a pulsatile response.

* * * * *